United States Patent
Karimi et al.

(10) Patent No.: US 6,813,374 B1
(45) Date of Patent: Nov. 2, 2004

(54) METHOD AND APPARATUS FOR AUTOMATIC IMAGE QUALITY ASSESSMENT

(75) Inventors: Seemeen S. Karimi, Malden, MA (US); David Rozas, Peabody, MA (US); Sergey Simanovsky, Brookline, MA (US); Ibrahim Bechwati, Roslindale, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 724 days.

(21) Appl. No.: 09/842,075

(22) Filed: Apr. 25, 2001

(51) Int. Cl.[7] .................................................. G06K 9/00
(52) U.S. Cl. .................................. 382/131; 378/207
(58) Field of Search .......................... 382/128, 131; 378/18, 207; 250/252.1, 453.11

(56) References Cited

U.S. PATENT DOCUMENTS

| | | | |
|---|---|---|---|
| 4,782,502 A | * 11/1988 | Schulz | 378/18 |
| 4,922,915 A | * 5/1990 | Arnold et al. | 128/653 R |
| 5,056,130 A | 10/1991 | Engel | 378/207 |
| 5,473,657 A | 12/1995 | McKenna | 378/4 |
| 5,802,134 A | 9/1998 | Larson et al. | 378/4 |
| 5,841,835 A | 11/1998 | Aufrichtig et al. | 378/207 |
| 5,953,444 A | * 9/1999 | Joseph et al. | 382/131 |
| 6,115,487 A | * 9/2000 | Toth et al. | 382/131 |
| 6,195,444 B1 | 2/2001 | Simanovsky et al. | 382/100 |
| 6,325,539 B1 | * 12/2001 | Bromberg et al. | 378/207 |

* cited by examiner

Primary Examiner—Andrew W. Johns
(74) Attorney, Agent, or Firm—McDermott Will & Emery LLP

(57) ABSTRACT

A method of and apparatus for assessing the image quality of a CT scanner is described in which assessment can be made manually or automatically. No special image quality mode of CT scanner operation is necessary, and no precise alignment of the phantom is necessary. In general, performance of the scanner comprises: using the scanner (a) to scan a phantom in one or more of its normal modes of operation while translating said phantom along the scanner axis of rotation and (b) to produce scanned data of the phantom, and assessing the performance of the scanner from the scanned data. In accordance with another aspect, the assessment is performed by (a) using the scanner to scan a phantom in one or more of its normal modes of operation; (b) reconstructing a three-dimensional volume CT image for a region containing at least a portion of the phantom; (c) calculating properties of the CT image; and (d) using the calculated properties of the CT image to assess CT scanner performance.

110 Claims, 10 Drawing Sheets

METHOD AND APPARATUS FOR AUTOMATIC IMAGE QUALITY ASSESSMENT

FIELD OF THE INVENTION

The present invention relates generally to computed tomography (CT) scanners, and more specifically to a method and apparatus to verify that a CT scanner meets its performance specifications.

Notation

For convenience of exposition, the following notations are used in the following specification:

AD Automatic Detection
CT Computed Tomography
FOV Field-of-view
IQP Image Quality Phantom
NSR Nutating Slice Reconstruction
ROI Region of Interest
SSP Slice Sensitivity Function (Profile)
MTF Modulation Transfer Function
z-axis Coordinate axis that coincides with axis of gantry rotation. The positive direction is the same as the direction of the gantry angular velocity vector.
x-axis Horizontal coordinate axis. The positive direction is to the right side of the gantry as viewed from the front face.
y-axis Vertical coordinate axis. The positive direction is upwards of the gantry is viewed from the front face. The x, y and z axes form a right handed system.
Axial slice Slice perpendicular to the z-axis
Sagittal slice Slice perpendicular to the x-axis
Coronal slice Slice perpendicular to the y-axis

BACKGROUND OF THE INVENTION

A CT scanner is a device used for manual or automatic discrimination of compositions, conditions or objects. In addition to traditional applications in medical imaging, non-medical applications for CT scanners are evolving. For example, baggage scanners using CT techniques have been proposed to search for contraband items such as explosives and narcotics in luggage at airports. Scanners for industrial testing have also been proposed.

One type of system using CT technology is a CT scanner of the third generation type, which typically includes an X-ray source and an X-ray detector system secured to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. Alternatively, the detector system can include a "two-dimensional" array of detectors disposed as multiple rows forming a cylindrical surface whose axis passes through the source. The X-ray source generates a fan-shaped beam (when used with a linear array of detectors) or cone-shaped beam (when used with a two-dimensional array of detectors) of X-rays that emanates from the focal spot, passes through an imaging field, and is received by the detectors. The CT scanner includes a predefined coordinate system, defined by mutually orthogonal X-, Y- and Z-axes, wherein the axes intersect and are all normal to one another at the center of rotation of the disk as the disk rotates about the rotation axis. This center of rotation is commonly referred to as the isocenter. The Z-axis is defined by the rotation axis of the scanner, and the X-and Y-axes intersect the Z-axis at the isocenter and are defined by and lie within the planar imaging field. The X, Y and Z-axes form a right handed system. The fan beam is thus defined as the volume of space existing between a point source, i.e., the focal spot, and the receiving surfaces of the detectors of the linear detector array exposed to the X-ray beam. In the case of the fan beam, because the dimension of the receiving surfaces of the linear array of detectors is relatively small in the Z-axis direction the fan beam is relatively thin in that direction. In a similar manner, the cone beam is defined as the volume of space existing between a point source, i.e., the focal spot, and the receiving surfaces of the detectors of the detector array exposed to the X-ray beam. Scanners have been developed for generating three dimensional images from the data acquired from a scan.

Each detector generates an output signal representative of the intensity of the X-rays incident on that detector during a sampling period. Since the X-rays are partially attenuated by all the mass in their path, the output signal generated by each detector is representative of the density of all the mass disposed in the imaging field between the X-ray source and that detector.

As the disk rotates, the detectors of the detector array are periodically sampled, and for each measuring interval each of the detectors in the detector array generates an output signal representative of the density of a portion of the object being scanned during that interval. The collection of all of the output signals generated by all the detectors of the detector array for any measuring interval is referred to as a "projection", and the angular orientation of the disk (and the corresponding angular orientations of the X-ray source and the detector array) during generation of a projection is referred to as the "projection angle". At each projection angle, the path of the X-rays from the focal spot to each detector, called a "ray", increases in cross section from a point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well known algorithms, a CT image of the object may be generated from all the projection data collected at each of the projection angles. Where the object is stationary during the scan (so called "constant axis" scanning), the CT image is representative of the density of a "two dimensional slice" of the object through which the X-ray beam has passed during the rotation of the disk through the various projection angles. When the object and rotating disk are moved relative to one another along the Z-axis (so called "helical" or "volumetric" scanning), a collection of data is acquired though a volumetric "slice" of the object through which the X-ray beam has passed during the rotation of the disk through the various projection angles. Multiple slices can be obtained in a "step-and-shoot" process, a mode of operation where successive "axial" slices are obtained from constant axis scans respectively at incremental positions of the gantry relative to the scanned object. Thus, step-and-shoot scanning is a mode of operation of the scanner in which projections for one axial slice or set of axial slices, are acquired without translating the object or patient and gantry during each axial scan. To get projections of another slice or set of slices, the patient and gantry are translated relative to one another before the next acquisition begins. There is no simultaneous imaging and translation as in helical scanning. Data from successive slices obtained from a step-and-shoot scan can be utilized to provide a volumetric image. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner.

Image processing techniques are known in the art for generating an image of the target object, slice by slice. Each slice is viewed as being composed of a plurality of individual volume elements. Information regarding the different amounts of x-ray attenuation by the different volume elements within each slice is used to determine the density and position of the internal structures that make up the slice. Each volume element is characterized by a numerical value, referred to as the CT number, which represents its attenuation characteristics. CT numbers are conventionally scaled relative to the x-ray attenuation coefficient of pure water, which is assigned a CT number equal to 0 under the Hounsfield scale that ranges from low density (about −1000) to high density (about +3095). The CT number of a material thus represents the attenuation coefficient of the material relative to the attenuation coefficient (0) of pure water. Soft tissues commonly have CT numbers in the range from about −1000 to about 500. The CT number for bone is about 800, whereas metals often have CT numbers in excess of 2000.

In some applications, it has been beneficial for the CT system equipment to automatically analyze the acquired density data and determine if the data indicate the presence of any contraband items, e.g., explosives in the case of non-medical applications, or any abnormality in the case of medical application. This automatic detection process should have a relatively high detection rate. At the same time, the false alarm rate of the system should be relatively low to substantially reduce or eliminate false alarms on innocuous items or conditions.

Systems used for discrimination of compositions, objects or conditions must provide the same (i.e. consistent and uniform) discrimination results for the same scanned compositions, objects and conditions, so that one set of algorithms and parameters may be used by all of the scanners. This requirement applies to any composition, object or condition that may be scanned. Therefore, the images provided by the scanners should be similar enough that the same discrimination results are obtained.

In order to ensure that a scanner meets specification in terms of its discrimination capabilities and other performance criteria, it is beneficial to test its image quality. It is additionally beneficial to perform automatic image quality testing on the scanner. Finally, it is beneficial to test the image quality performance in a mode in which the scanner is normally operated. A normal operating mode, also referred to as normal mode, is defined herein as the mode of operation of the scanner for its application. For example, in a medical scanner, for some applications, a scanner may be operated with some protocol comprising some combination of helical scanning pitch, gantry speed, dose rate and reconstruction method. If the image quality can not be assessed in the normal mode of operation, or if there are several normal modes that produce images with different image quality, and only one is tested, then the performance may not be accurately assessed. A non-normal mode may have different scanning pitch, gantry speed, use a different reconstruction algorithm and/or different reconstruction parameters.

Specific phantoms are known to be used to evaluate the performance of CT scanners in terms of image quality. All the phantoms are designed for step-and-shoot scanning. There is no simultaneous imaging and translation as in helical scanning.

A common type of phantom, known as the "wedding cake" phantom, comprises multiple stacked disks of different diameters. Each disk contains inserts for specific measures of image quality. The various inserts, such as comb phantoms, wires, and low contrast objects, are in separate disks so that they are scanned separately, to prevent artifacts caused by one insert from corrupting the measurements of another insert.

The image quality assessment method by Engel et al., entitled "Computerized Tomography Calibrator," U.S. Pat. No. 5,056,130, and a method by Aufrichtig et al., entitled "Apparatus and Methods for Automatic Monitoring and Assessment of Image Quality in X-ray systems," U.S. Pat. No. 5,841,835, represent , prior art in the field of image quality assessment. These methods require precise positioning of the phantom, step-and-shoot scanning, and special, non-normal modes of operation. These are some of the problems addressed by the present invention.

SUMMARY OF THE INVENTION

The present invention is directed to an apparatus for and method of processing computed tomography data for a region to assess the performance of the scanner in any of its normal modes of operation.

In one embodiment, the scanner is an explosives detection scanner ("EDS"), which has only one mode of normal operation, with a conveyor belt operating at a fixed conveyor speed (for transporting objects through the scanner), a disk rotating at a substantially fixed gantry speed, and the software including a fixed reconstruction algorithm and parameters. The image quality phantom (IQP) is manually placed on the conveyor belt of the EDS scanner for scanning, such that precise positioning of the phantom is neither possible nor necessary.

The image quality phantom is of a predetermined shape, configuration and composition, with a plurality of predefine inserts. The inserts are specially designed so that certain properties can be measured from CT images.

In one embodiment the phantom is scanned so as to reconstruct a 3-dimensional image from CT data of the phantom, and using an auto-detection (AD) computer, objects are identified and matched with the inserts, properties of the identified objects are measured, and the identified objects are compared with the known properties of the known inserts, so that the ability of the CT scanner to faithfully capture the properties can be assessed.

In one embodiment of the invention, the assessment verifies the following:
 1. The stability of the high voltage power supply that powers the X-ray tube (hereinafter referred to as "X-ray tube voltage").
 2. The X-ray flux.

3. The placement of the conveyor belt relative to the scanner.
4. The speed of the gantry.
5. The speed of the belt.
6. The communication with the AD computer.
7. The AD computer discrimination performance including its parameters.

In one embodiment the IQP comprises a suitcase preferably made of plastic with inserts that are specially designed for the tests listed above. The inserts preferably comprise objects of known size, shape and density, for example, cylinders of Nylon, Teflon and PVC, comb phantoms, a diagonal rod and a sheet explosive simulant. The object sizes are selected for the fixed pixel size of the CT image, which is determined by the normal mode of scanner operation. The objects for measuring CT number stability and noise are preferably cylindrical to make them suitable for the lack of precise positioning.

In one embodiment, the X-ray tube voltage stability is verified by measuring the CT numbers corresponding to the various known densities of the objects provided in the phantom, e.g., Nylon, PVC and Teflon are suitable materials. The placement of the conveyor belt within the field of view is preferably measured by finding the position and orientation of the IQP within the reconstructed images. The photon flux is preferably verified by measuring noise in the difference between two images of one of the types of objects, e.g., Nylon. The communication is preferably verified by ensuring that no slices are missing using a specific type of object whose relative position with a slice image changes with each successive slice. For example, a diagonal rod whose position in each successive slice can be predicted with the knowledge of the phantom and its position in each slice image. The AD computer discrimination is preferably verified by running AD software on the images, and using simulants that exercise the pathways of the AD software. In one embodiment, the entire assessment is done automatically on a computer, although it can be done manually. The software identifies the location of the IQP in the image, and determines the validity of the scan upon which to base the conclusions about the scanner.

In one embodiment, the system identifies multiple objects within the 3-D image, by combining voxels that match in CT number and locations. Regions of interest within these objects are identified by the software which are used to measure the properties of mean and standard deviation. The system preferably identifies the axial and sagittal slices within which to measure Slice Sensitivity Function (Profile) (hereinafter "SSF") and Modulation Transfer Function (hereinafter "MTF"), and measures the SSP and MTF by measuring the modulation that is obtained in the slices.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same or similar parts throughout the different views. The drawings are not necessarily to scale, emphasis instead being placed upon illustrating the principles of the invention.

DETAILED DESCRIPTION OF THE DRAWINGS

One embodiment of the invention is incorporated in a CT baggage scanning system of the type described and claimed in U.S. Pat. No. 6,195,444 issued Feb. 27, 2001 to Sergey Simanovsky, et al. and entitled "Apparatus and Method of Detecting Concealed Objects in Computed Tomography Data, which is assigned to the present assignee and incorporated herein in its entirety by reference. It should be appreciated, however, that the invention can be utilized with any CT scanning system of the type including a conveyor which transports objects through the scanner, or in which the scanner is translated relative to objects being scanned.

Figure 1:
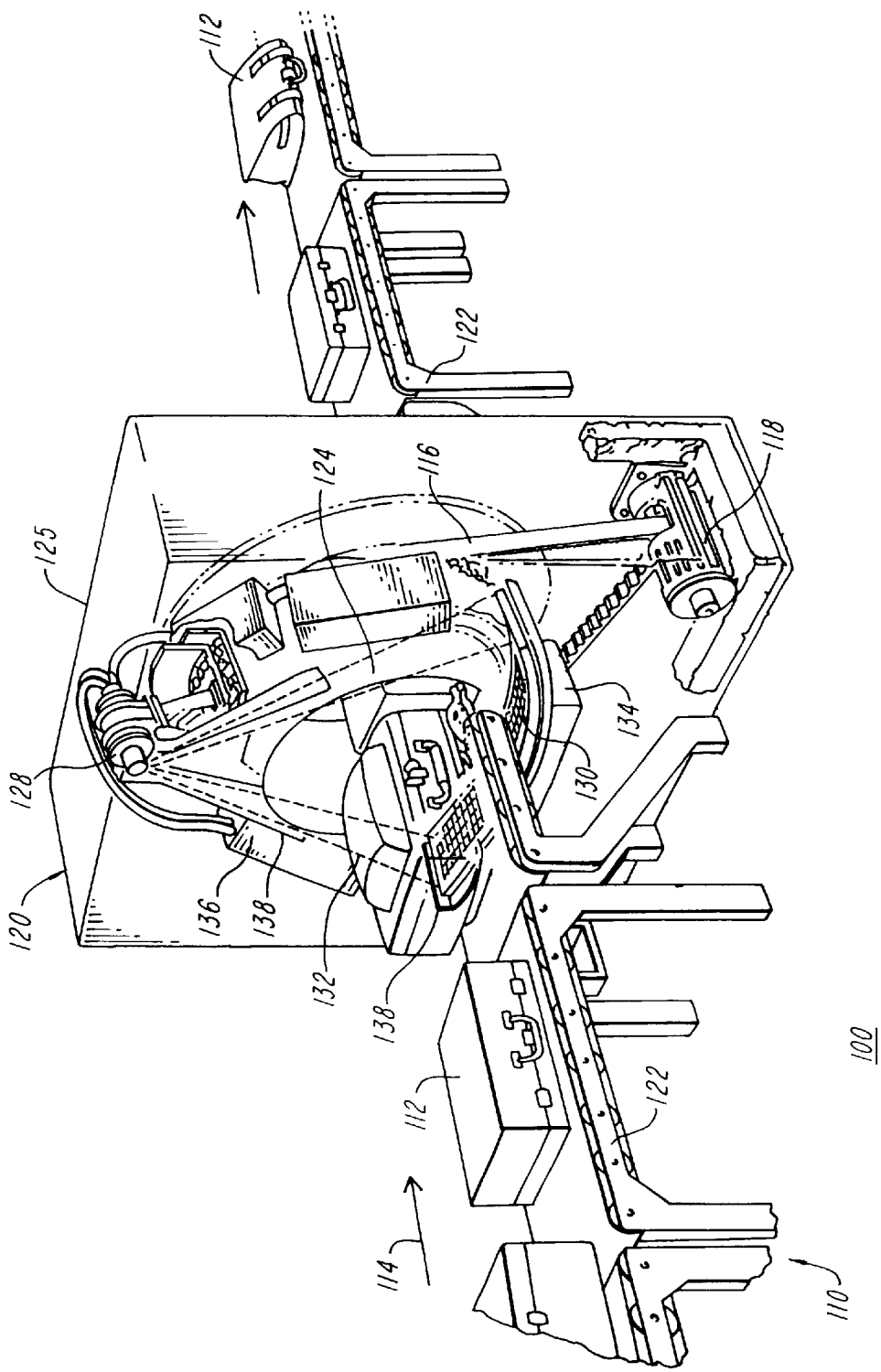
FIG. 1 is a perspective view of an embodiment of a baggage scanning system in accordance with the present invention, although the AD computer is not shown in this FIG.
Figure 2:
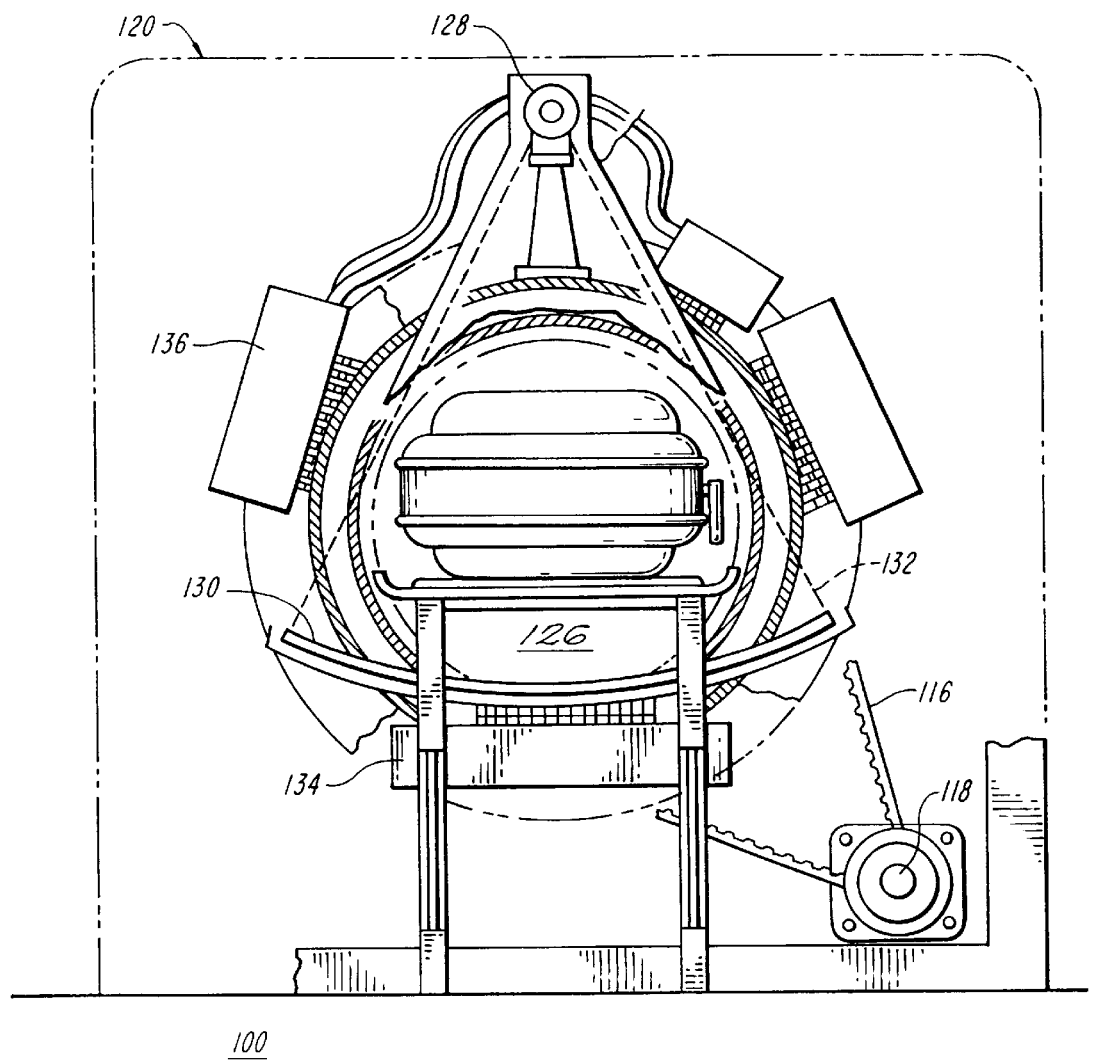
FIG. 2 is a cross-sectional end view of the system shown in FIG. 1.
Figure 3:
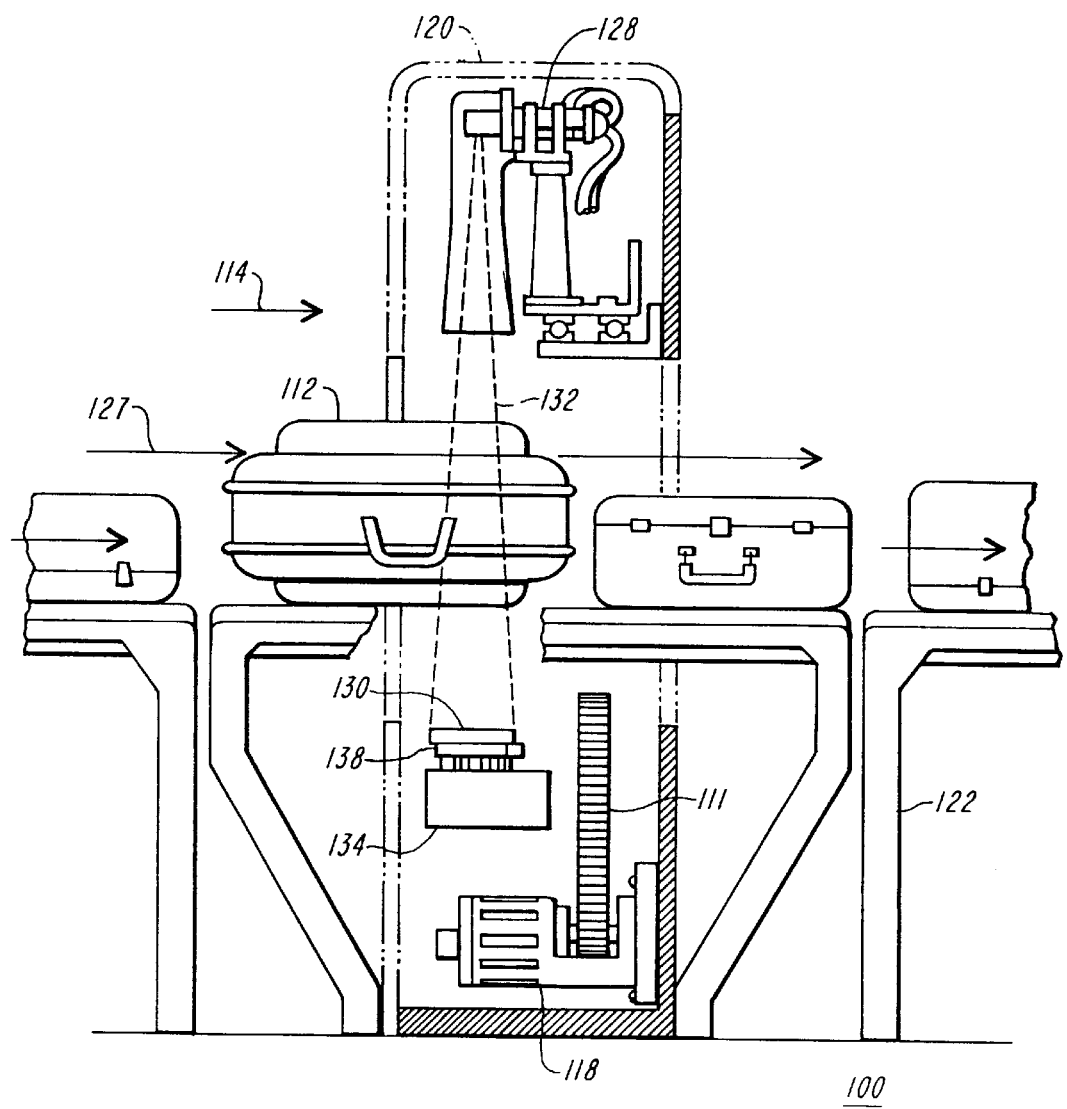
FIG. 3 is a cross-sectional radial view of the system shown in FIG. 1.

FIGS. 1, 2 and 3 contain perspective, end cross-sectional and radial cross-sectional views, respectively, of a baggage scanning system 100 constructed in accordance with the invention, which provides object detection, identification, and/or classification in accordance with the invention. The baggage scanning system 100 generates CT data for a region which can include a piece of baggage. The system can use the CT data to generate image volume elements or "voxels" for the region.

The system 100 includes a conveyor system 110 for continuously conveying baggage or luggage 112 in a direction indicated by arrow 114 through a central aperture of a CT scanning system 120. The conveyor system preferably includes motor driven belts for supporting the baggage. Conveyor system 110 is illustrated as including a plurality of individual conveyor sections 122; however, other forms of conveyor systems may be used.

The CT scanning system 120 includes an annular shaped rotating platform or disk 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as those described in the above-identified applications, or the one described in U.S. Pat. No. 5,473,657 issued Dec. 5, 1995 to Gilbert McKenna and entitled "X-ray Tomographic Scanning System," which is assigned to the assignee of the present application and which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 is preferably a two-dimensional array (although the invention could be used with a scanner of the type having a linear array of detectors). The system 120 further includes a data acquisition system (DAS) 134 for receiving and processing CT data signals generated by detector array 130, and an X-ray tube control system 136 for supplying power to, and otherwise controlling the operation of, X-ray tube 128. The system 120 is also preferably provided with a computer processing system for processing the output of the data acquisition system 134 and for generating the necessary signals for operating and controlling the system 120. The computer system can also include a monitor for displaying information including generated images. The X-ray tube control system 136 can be a standard X-ray control system, or alternatively, a dual-energy X-ray control system. Dual energy X-ray techniques for energy-selective reconstruction of X-ray CT images are particularly useful in indicating a material's atomic number in addition to indicating the material's density, although it is not intended that the present invention be limited to this type of control system. It is noted that the detailed description herein of the invention describes the details in connection with single-energy data. It will be understood that the description is applicable to multiple-energy techniques. System 120 also includes shields 138, which may be fabricated from lead, for example, for preventing radiation from propagating beyond gantry 125.

In one embodiment, the X-ray tube 128 generates cone beam 132 of X-rays that pass through a three-dimensional imaging field, through which baggage 112 is transported by conveying system 110. After passing through the baggage disposed in the imaging field, cone beam 132 is received by detector array 130 which in turn generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the baggage is continuously transported through central aperture 126 by conveyor system 110 so as to generate a plurality of projections at a corresponding plurality of projection angles.

In a well known manner, signals from the detector array 130 can be initially acquired by data acquisition system 134, and subsequently processed by a computerized processing system using CT scanning signal processing techniques. The processed data can be displayed on a monitor, and/or can also be further analyzed by the processing system as described in detail below to determine the presence of a suspected material or for machine performance analysis. For example, the CT data can be analyzed to determine whether the data suggest the presence of material having the density (and when a dual energy system is used, molecular weight) of explosives. If such data are present, suitable means can be provided for indicating the detection of such material to the operator or monitor of the system, for example, by providing an indication on the screen of the monitor by sounding an audible or visual alarm, and/or by providing an automatic ejection device (not shown) for removing the suspect bag from the conveyor for further inspection, or by stopping the conveyor so that the suspect bag can be inspected and/or removed.

As stated above, detector array 130 can be a two-dimensional array of detectors capable of providing scan data in both the directions of the X- and Y- axes, as well as in the Z-axis direction. During each measuring interval, the plurality of detector rows of the array 130 generate data from a corresponding plurality of projections and thereby simultaneously scan a volumetric region of baggage 112. The dimension and number of the detector rows are preferably selected as a function of the desired resolution and throughput of the scanner, which in turn are a function of the rotation rate of rotating platform 124 and the speed of conveying system 110. These parameters are preferably selected so that in the time required for a single complete rotation of platform 124, conveying system 110 advances the baggage 112 just enough so that the volumetric region scanned by detector array 130 during one revolution of the platform is contiguous and non-overlapping with (or partially overlapping with) the volumetric region scanned by detector array 130 during the next revolution of the platform.

Conveying system 110 continuously transports a baggage item 112 through CT scanning system 120, preferably at constant speed, while platform 124 continuously rotates at a constant rotational rate around the baggage items as they pass through. In this manner, system 120 preferably, although not necessarily, performs a helical volumetric CT scan of the entire baggage item. Baggage scanning assembly 100 preferably uses at least some of the data provided by the array 130 and a helical reconstruction algorithm to generate a volumetric CT representation of the entire baggage item as it passes through the system. In one embodiment, the system 100 performs a nutating slice reconstruction (NSR) on the data as described in U.S. Pat. No. 5,802,134 issued Sep. 1, 19998 to Carl Crawford, et al. and entitled "Nutating Slice CT Image Reconstruction Apparatus and Method,". The system 100 thus preferably provides a complete CT scan of each bag, rather than only providing CT scanning of selected portions of baggage items, without the need for a pre-screening device. The system 100 also provides rapid scanning since two-dimensional detector array 130 allows the system 100 to simultaneously scan a relatively large portion of each baggage item with each revolution of the platform 124.

Figure 4:
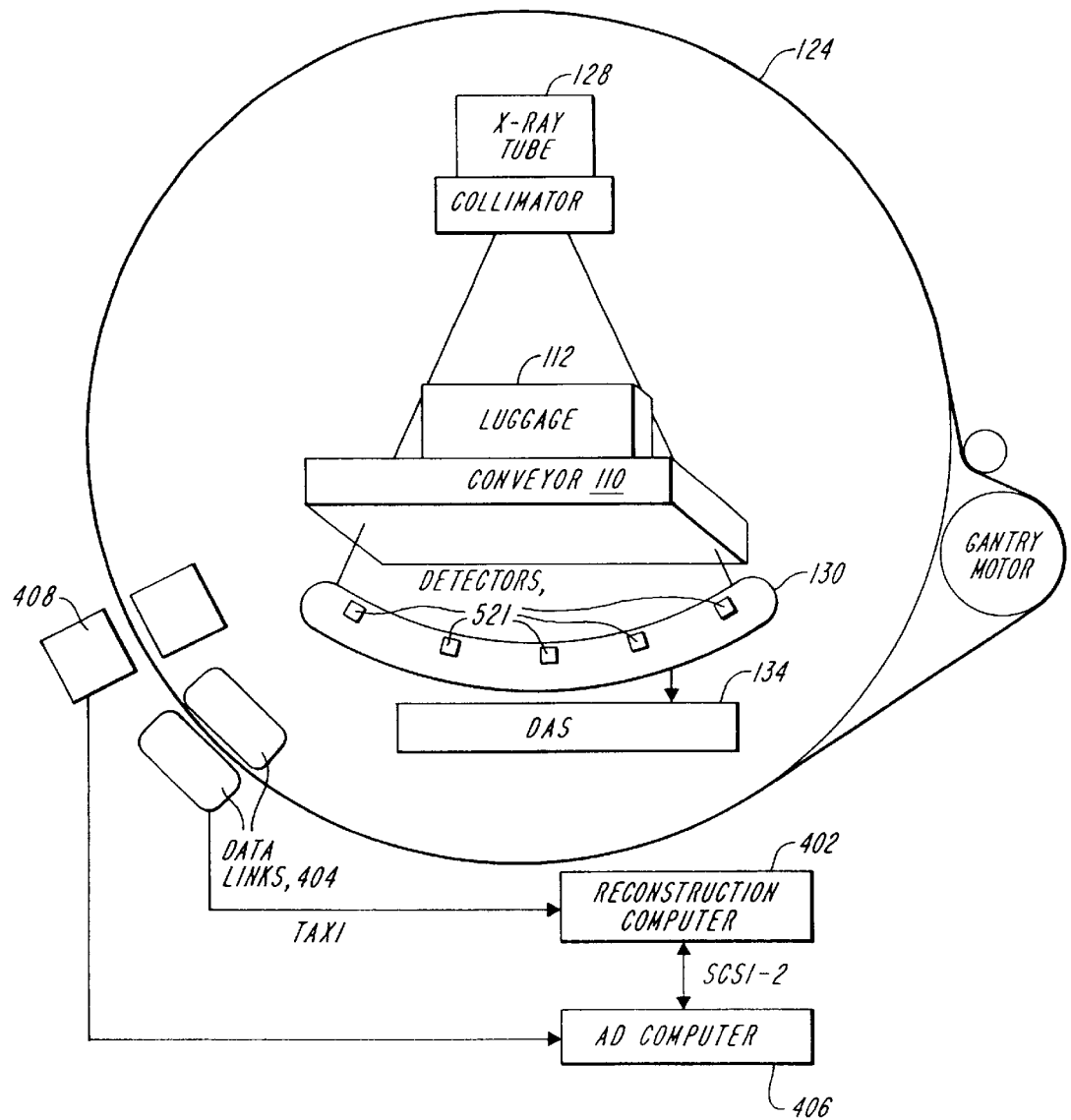
FIG. 4 is a schematic electrical and mechanical block diagram of one embodiment of the baggage scanner of the invention, wherein the AD computer is included.

FIG. 4 contains a mechanical/electrical block diagram of one embodiment of the baggage scanning system 100 of the invention. The mechanical gantry of the scanner 100 includes two major components, the platform, in the form of a disk 124, and a frame forming the gantry support (not shown in FIG. 4, but shown in FIGS. 1–3 at 125 ). Among other things disk 124 is the rotational element which carries the X-ray source assembly 128, the detector assembly 130, and the data acquisition system (DAS) 134. The frame supports the entire system 100, including the baggage handling conveyor system 110. The disk 124 is mechanically connected to the frame via a suitable drive mechanism.

In one embodiment, the baggage conveyor system 110 includes a single belt driven at a constant rate to meet specified throughput requirements. The belt can be driven by a high-torque, low-speed assembly to provide a constant speed under changing load conditions. A low-attenuation material is used for the portion of the conveyor bed exposed to X-rays. The total length of the conveyor is designed to accommodate at least three average length bags, although the length is not critical to the present invention, and therefore can vary to accommodate as little as one bag to as many bags as desired. The conveyor preferably extends through a tunnel to meet the appropriate safety requirements of a cabinet X-ray system.

In operation, the dual-energy X-ray photons strike the baggage as it passes through the machine, and some portion of the X-rays pass through the baggage and strike the detector assembly 130. The detector assembly 130 performs an analog conversion from X-ray photons to an electrical signal. The DAS 134 can sample and amplify the detector signals, multiplex the amplified signals to a set of analog-to-digital converters and multiplex the digital outputs to the computerized processing system or reconstruction computer 402, which generates CT data and performs AD, as described, for example, in U.S. Pat. No. 6,195,444, referenced above. In one embodiment, the digital data from the DAS 134 are transferred to the processing system 402 via a data link 404. The DAS 134 can be triggered by the angular position of the disk 124.

In one embodiment, the image reconstructor portion of the processing system 402 converts the digital line integrals from the DAS 134 into a set of two-dimensional images of object slices for both the high and low energies. The CT reconstruction can be performed via a helical-cone-beam solution, such as the nutating slice reconstruction method described in U.S. Pat. No. 5,802,134, referenced above. The reconstructor portion can include embedded software, a high-speed DAS port, an array processor, a DSP-based convolver, an ASIC-based backprojector, image memory, UART control port, and a SCSI output port for image data. The array processor can perform data corrections and interpolation. The reconstructor can be self-hosted and can tag images based upon the baggage information received over the UART interface to the frame computer.

The processing system 402 can include a PC-based embedded control system. This system can also have a video and keyboard interface for engineering diagnostics and control. Additionally, a control panel can be included for field service. An AD computer 406 is provided with suitable software for performing the autodetection process.

The, ability to use the CT scanner to obtain correct discrimination results is assessed based upon the images created by the CT scanner of known objects. Further, the ability of the system including the AD computer 406, in FIG. 4, to perform automated detection is also assessed by scanning special inserts for this purpose. The AD computer 406 communicates with the rest of the scanner via a link 408. It should be appreciated that while FIG. 4 shows processing system 402 and AD computer 406 as separate computers linked together, the functions of both can be performed by a single computer.

Figure 5:
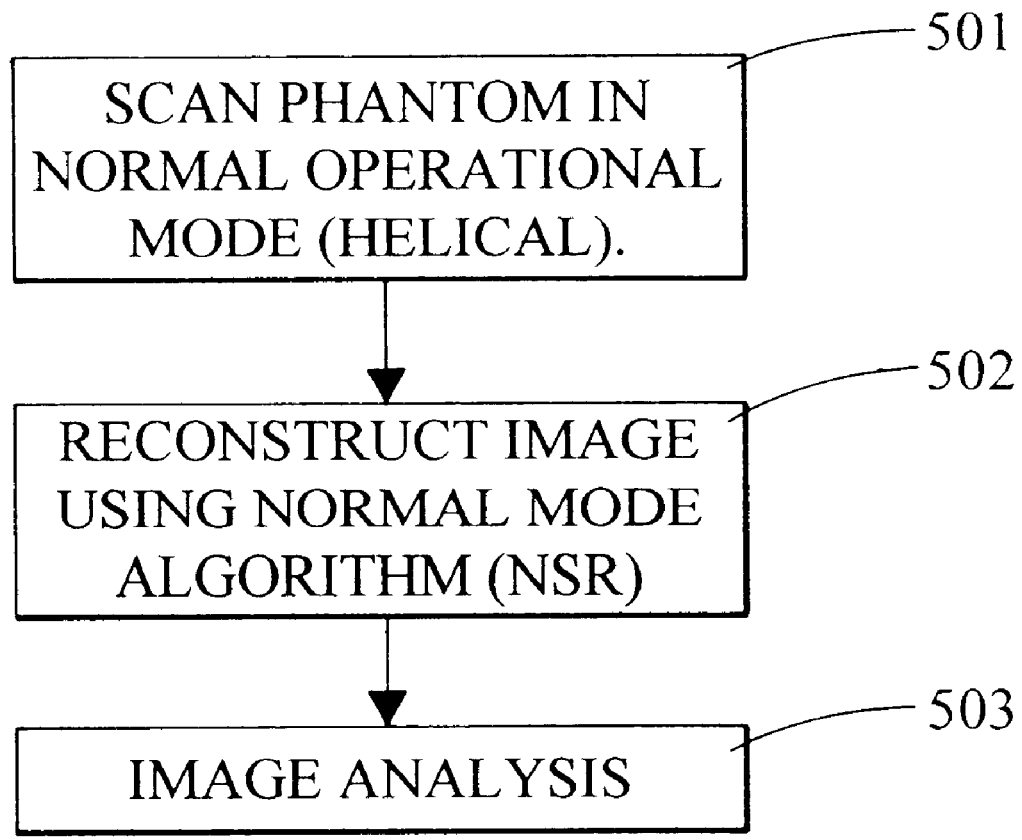
FIG. 5 is a logical flow diagram of one embodiment of the top-level process of the invention, with some of these blocks expanded in subsequent FIGS.

The preferred embodiments of the image quality (IQ) assessment method of the present invention is described in a hierarchical manner, in progressively deeper levels of detail. A block diagram of the entire testing process is shown in FIG. 5. The blocks are further expanded in the next level of detail, described with respect to FIGS. 6 and 7. Certain blocks from FIG. 7, describing complicated functions are described in the next level of detail in FIGS. 8, 9 and 10.

FIG. 5 shows one embodiment of the logical blocks of the basic steps of the IQP assessment method used in connection with the baggage detection system described in this application. In this embodiment, the scanner is a helical scanner, and the analysis of CT images is done automatically.

Block 501 denotes scanning the IQP, in a normal operation mode of the scanner. In this embodiment normal denotes helical scanning with a fixed pitch and fixed voxel size, as it is used in the detection of objects. The IQP must be generally aligned with the axis of the scanner. Precise positioning is not required in this invention, nor possible in the scanner embodiment described here. It is not possible because the IQP can only be placed on the conveyor system, not directly within the X-ray beam. There is variability in the electrical and mechanical components too, both in the conveyor system and in the system which senses the presence of a bag in the scanner and triggers reconstruction.

Block 502 denotes image reconstruction to create a 3-dimensional image. The normal reconstruction technique in this embodiment is preferably the nutating slice reconstruction (NSR) algorithm described in U.S. Pat. No. 5,802,634, with fixed parameters such as voxel size, nutation angle and scaling constants.

Block 503 denotes image analysis on the AD computer 406. The outcome of each image analysis step is in the form of a binary decision that indicates the acceptability of the scanner as a device for discrimination.

Figure 6:
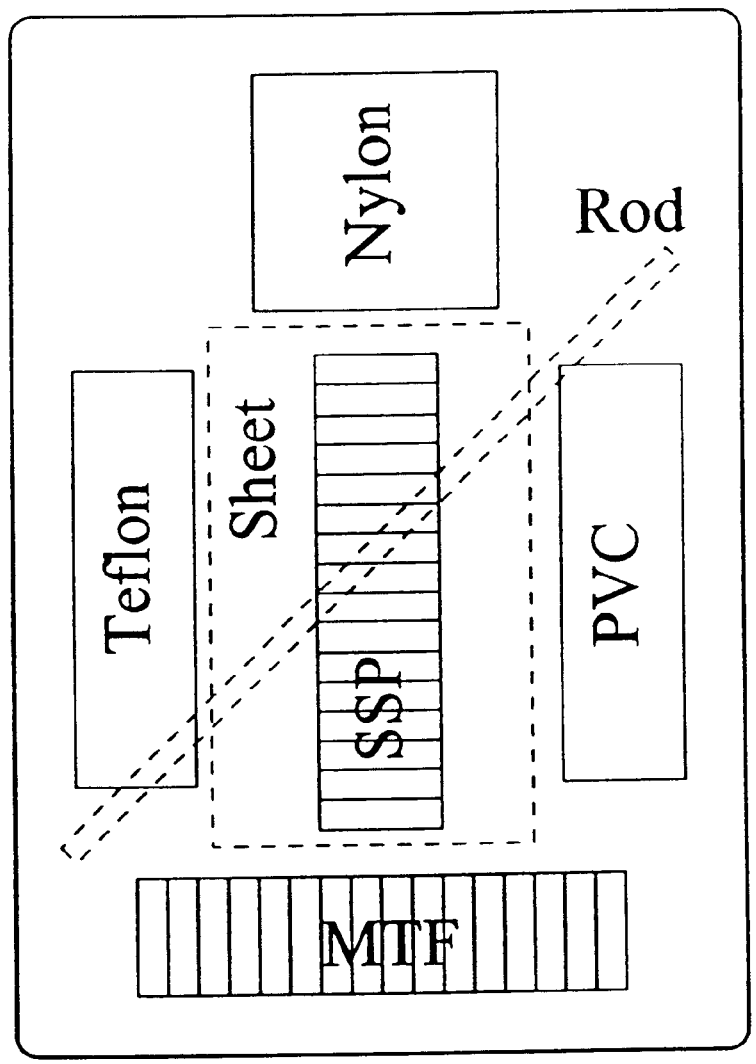
FIG. 6 is a simplified top view diagram of one embodiment of the phantom of the invention.

FIG. 6 shows one embodiment of the IQP. The IQP preferably comprises a plastic suitcase. The suitcase is filled with foam in which cut-outs are made. Inserts of various sizes, shapes and known materials are preferably placed in the cut-outs and held in place by the foam. The inserts are thus placed in known preselected locations relative to one another. The inserts are positioned to minimize contamination from one object to another in the reconstructed images, i.e, minimize the affects of imaging one insert with the imaging of any of the other inserts. The inserts are described below in their preferred embodiment with respect to the shapes, sizes and material of each, although the particular sizes, shapes and materials can vary depending on such variables as the size of the FOV.

1. A Nylon cylinder used for measurement of noise and X-ray tube voltage stability. By way of example, it has a diameter of 8 inches and length of 8.5 inches. It is also used to test AD software used with the AD computer 406.

2. A polyvinyl chloride (PVC) cylinder used for the measurement of X-ray tube voltage stability. By way of example, it has a diameter of 3.5 inches and length of 11 inches. It is also used to test AD software.

3. A Teflon cylinder is used for the measurement of X-ray tube voltage stability. By way of example, it has a diameter of 3.5 inches and length of 11 inches. It is also used to test AD software.

4. A comb insert used for the measurement of axial resolution (MTF). The phantom has multiple groups of plastic fins, for example seven, mounted in a plastic frame, although the number fins can vary. By way of example, the fin groups have spacing as follows: 1.0 lp/cm, 1.2 lp/cm, 1.4 lp/cm, 1.6 lp/cm, 1.8 lp/cm, 2.25 lp/cm and 2.75 lp/cm.

5. A comb insert for measurement of slice sensitivity profile (SSP). The insert is identical to the one used for MTF.

6. A diagonal aluminum rod used for testing communication between the scanner and AD computer. By way of example, it has a diameter of 0.5 inches and length of 20 inches.

7. A rubber sheet which is a sheet explosive simulant, used to test the AD software. By way of example, it has a length of 13 inches, width of 10.5 in and a thickness of 0.5 inches.

Figure 7:
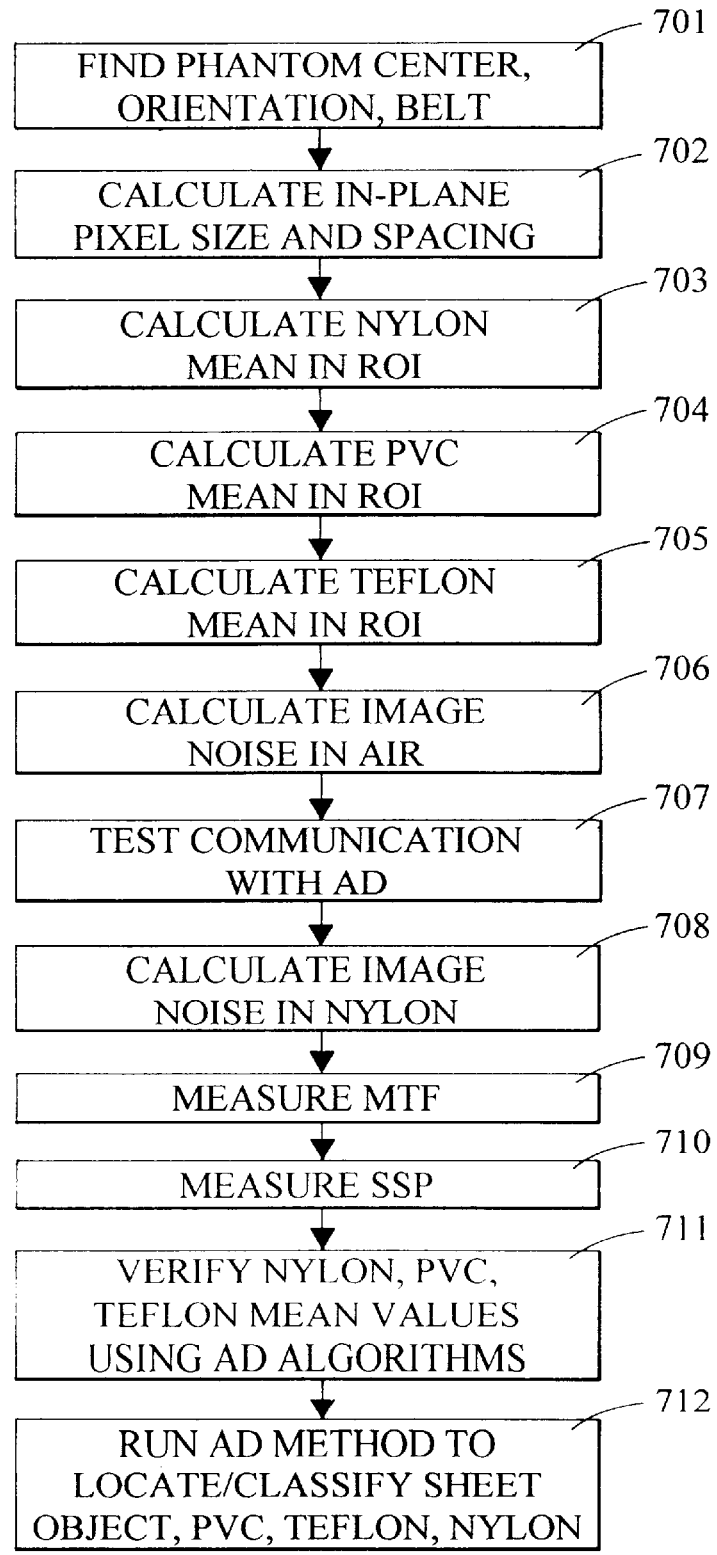
FIG. 7 is a logical flow diagram of one embodiment of a process of image analysis.

FIG. 7 shows a logical block diagram of the process of automatic image analysis. The outcome of each process block is a pass/fail result of the particular test that the block represents. Each of the image analysis steps tests some part of the scanner, so that the scanner is considered to meet the image quality performance requirements if all tests are passed. If not, the outcome indicates to the user what subsystem of the scanner is likely to be faulty. The significance of each step is given in the following paragraphs explaining FIG. 7.

Block 701 denotes the step of locating the phantom in the image and a test for belt position of the conveying system 110. The position of the center of the phantom, e.g., the suitcase, and orientation of the phantom is determined. If the position and orientation information indicates that a portion of the phantom is outside the scanner FOV, then the method of the invention rejects the scan, because the image may not be suitable for further analysis. In one particular embodiment, where the FOV has a radius of 40 cm, the phantom has to be generally centered within 10 cm of the center of the FOV, and its long dimension must be generally aligned with the z-axis to within 10 degrees. These numbers can vary. The position of the belt is also measured. The height of the belt must be within predetermined upper and lower thresholds. The belt location is determined by the location of the phantom, because the phantom rests on the belt. If the belt position is outside the predetermined upper and lower thresholds, then the test for belt position fails.

Block 702 represents two tests. The first is finding the in-plane pixel size (the area in each slice plane represented by a pixel in the image) and the second is finding slice spacing (the spacing represented by images of the two adjacent slice planes). These two tests are a measure of any distortion of the image. The distortion could be caused by variation in belt or gantry speed, since the parameters of the NSR algorithm expect certain fixed values of belt and gantry speed.

Two objects of different atomic number are used to test the X-ray spectrum. Block 703 represents X-ray voltage stability measurement from the CT number of the nylon phantom. The image object representing the nylon cylinder is located. A region of interest (ROI) is located in the object. The mean CT number within the ROI is found and compared with predetermined upper and lower threshold values. If the mean CT number is within the threshold values, the test is passed, i.e. the X-ray voltage is considered stable.

Block 704 represents X-ray voltage stability measurement from the CT number of a PVC cylinder. The PVC cylinder is located within the image based on its known relative position in the phantom, and a ROI is identified within the PVC cylinder. The mean CT number within the ROI is calculated and compared with threshold values.

Block 705 represents X-ray voltage stability measurement from the CT number of a Teflon cylinder. The position of the Teflon cylinder within the image is found based upon its known relative position within the phantom, and a ROI is identified within the Teflon cylinder. The mean CT number within the ROI is calculated and compared with predetermined threshold values. Using various materials assesses the spectrum of the X-rays.

Block 706 represents the test for artifacts in air images by measuring the noise (standard deviation). The mean and standard deviation of CT numbers in a ROI are calculated from a slice containing only air. The presence of any artifacts indicates instability in the detector/DAS subsystems or the presence of objects in the FOV. If the standard deviation is too high, i.e., above a predetermined threshold, that indicates artifacts, and the test fails.

Block 707 represents the testing of communication of the scanner with the AD computer. The diagonal rod is located in a slice using the knowledge of the location of the phantom from Block 701, and the knowledge of the phantom design. The diagonal rod in each axial slice is located and compared with a predicted location. If the rod has moved from its predicted location, then axial slices may be missing or out of order. The number of slices missing can be determined from the distance between the predicted and measured locations.

Block 708 represents the test for X-ray flux by image noise measurement using the nylon cylinder. Noise is calculated to estimate the photon flux, i.e. whether the X-ray intensity is correct, and whether there are sources of noise other than statistical variation in X-ray emission. Since reconstruction is deterministic, and verified by the previous tests, the noise in the data has a fixed relationship with the noise in the image in the absence of artifacts. Noise is calculated as the standard deviation in the difference of two slices reconstructed from data one rotation apart. The slices must have this separation to subtract out the artifacts which would otherwise contribute to the standard deviation measurement. Noise is usually calculated as the difference of two slices scanning the same data. However, this would require exact repeatability of the scan which is not possible because of the reasons given earlier. The need for exact repeatability is avoided sufficiently, however, by using a slice pair one rotation apart.

Block 709 represents the measurement of the MTF. Modulation in an axial slice though the comb phantom labeled MTF in FIG. 6 is computed. The definition and measurement of the MTF is described hereinafter, and illustrated in FIG. 10.

Block 710 represents the measurement of the SSP. Modulation is computed in a sagittal slice through the comb phantom mounted parallel to the IQP length axis to determine results for the SSP test. Modulation is measured in the same way as for the MTF test. It should be appreciated that in the prior art, SSP is usually measured with a bead phantom by reconstructing overlapping slices. Using the (fixed) reconstruction parameters in the normal mode of scanner operation, overlapping slices are not possible, therefore insufficient sampling would lead to aliasing and inaccurate measurement using a bead phantom. It is also known in the prior art to measure the SSP using a slanted wire phantom. However, when the SSP and MTF are close in magnitude, then the MTF contaminates the measurement of the SSP. It is not known in the prior art to use comb phantoms to measure the MTF of CT scanners. The SSP from a step and shoot system is nearly rectangular, and its Fourier transform is a sinc function with infinite frequency content. Therefore it cannot be measured using a comb phantom which is also a sinc function with infinite frequencies. The preferred embodiment of the method of present invention uses a comb phantom to measure SSP in a helical mode, which has a smooth non-rectangular SSP.

Block 711 represents the testing of Nylon, PVC and Teflon mass and density (both of which are predetermined and therefore known) using the methods in the AD algorithms. These test the AD software.

Block 712 represents a discrimination task using the rubber sheet. The AD algorithms are used to find the sheet and assess whether it is a threat. This test is used to test the AD algorithm.

The preferred techniques of finding the position and orientation of the suitcase, measuring the Nylon, PVC, and Teflon mass and density, and the MTF and SSP measurements are described in greater detail below. Each of these techniques is represented as a logical block diagram of its own. The rationale for choosing the particular phantom, and the approach of the test are also described along with the description of the process.

Figure 8:
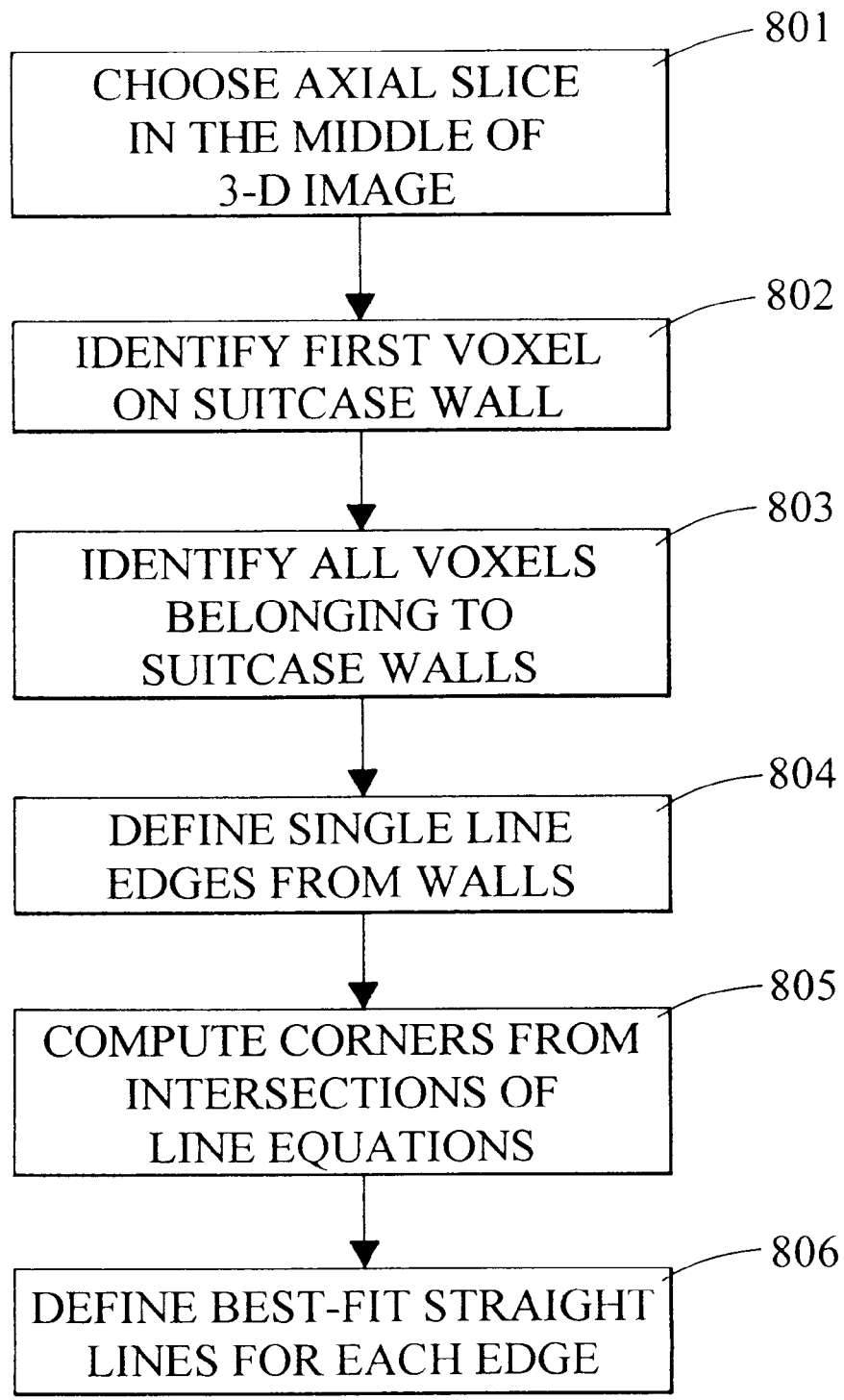
FIG. 8 is a detailed logical flow diagram of the first step of one embodiment of an image analysis which is to locate the phantom in the image.

FIG. 8 shows the preferred embodiment of the process that represents Block 701 in FIG. 7. Locating the phantom comprises the steps of locating one voxel belonging to any suitcase wall, growing this voxel to find all the walls of the suitcase, and averaging the coordinates from the set of voxels representing the suitcase walls, to give center coordinates.

The step of finding the orientation of the phantom preferably uses a single axial slice. The axial slice is chosen based on the center coordinates, and the knowledge of the phantom. Finding the orientation comprises the steps of finding single-pixel edges to represent walls of the suitcase in the slice, characterizing the edges by a set of best fit straight lines, and finding the intersections of the straight lines to find the corners.

In FIG. 8, Block 801 represents finding any one wall of the suitcase. This is accomplished by choosing the axial slice number equal to half the number of slices in the 3-D image, and searching each row from first to last column until a pixel with a CT number value greater than a predetermined minimum threshold $\rho_{thresh}$ is found. This voxel is assumed to lie in the suitcase side, and is referred to herein as a "seed" voxel.

Block 802 of FIG. 8 represents identifying all voxels in the image that belong to the suitcase. This is accompanied by face-adjacent region growing, for which the algorithm is given below. Any type of connected-components labeling (CCL) algorithms can be used to do this task.

The following are the steps for region growing in an image defined as C(i,j,k), were i,j, and k are voxel indices.

1. Provided with the coordinates of a seed voxel within the image C(i,j,k), the CT number values of all 6 face adjacent voxels are reveiwed. If the CT number value of the $n^{th}$ neighboring voxel is greater than or equal to $\rho_{thresh}$, the voxel's address is pushed onto a stack.
2. Once all 6 neighbors of the voxel have been reviewed, the top voxel on the stack is popped. The address of this voxel T is then stored in a copy image, $C_{copy}(i,j,k)$.
3. The six neighbors of T in the original image, C(i,j,k), are then reviewed if and only if they have not been stored in the copied image, $C_{copy}(i,j,k)$.
4. Any voxels scanned in step 3 with CT number values greater than or equal to $\rho_{thresh}$ are pushed onto a stack.
5. Repeat from step 2 until the stack has been exhausted.

The coordinates of all nonzero voxels in $C_{copy}(i,j,k)$ are averaged as follows.

$$\begin{pmatrix} \bar{i} \\ \bar{j} \\ \bar{k} \end{pmatrix} = \frac{1}{N_c} \sum_{n=1}^{N_c} \begin{pmatrix} i_n \\ j_n \\ k_n \end{pmatrix} \tag{1}$$

where $i_n$, $j_n$ and $k_n$ represent the x, y, and z coordinates of the $n^{th}$ voxel in $C_{copy}(i,j,k)$ respectively, and $N_c$ represents the number of nonzero voxels in $C_{copy}(i,j,k)$.

The averaged coordinates $\bar{i}$, $\bar{j}$, and $\bar{k}$ are the coordinates used to represent the center of the IQP.

Block 803 represents choosing an axial slice for the computation of orientation and position of the phantom in the field of view.

Block 804 represents the step of finding lines to represent the walls of the phantom. This step can be accomplished by searching from the image edge to the wall of the suitcase. Linear interpolation between the pixel greater than the threshold $\rho_{thresh}$ and the one below the threshold gives a floating point y-coordinate for each column, for the top and bottom sides, and a floating point x-coordinate for each row for the left and right sides. The calculation of the floating point y-coordinate given the x-coordinate for the top or bottom edge is as follows.

$$j_{float} = \frac{\rho_{thresh} - S(i,j)}{S(i,j) - S(i,j^-)} + j \tag{2}$$

where the first point over the threshold $\rho_{thresh}$ in the direction of the search has coordinates (i,j) and CT number value S(i,j), and the preceding pixel (CT number value lower than $\rho_{thresh}$) has coordinates (i,j$^-$) and CT number value S(i,j$^-$)

Block 805 represents characterizing the four sides of the suitcase by straight lines. This is accomplished using the Hough transform and a clustering method, as described below.

A line is characterized by two parameters. The first is the angle of the normal to the line passing through the origin (of the coordinate system where i=0, j=0 and k=0), and the second is the distance of the line from the origin. For each point on the suitcase edge, a set of lines passing through the point is identified. Each line in the set is marked as a point in the Hough Transform space. The point has two coordinates defining the line, the distance and angle of its normal, from the origin.

$$r_k = x_n \cos\theta_l + y_n \sin\theta_l \tag{3}$$

where $(x_n, y_n)$ are the coordinates of a point in image space.

Equation ($_3$) gives the distance of a line from the origin, $r_k$ for a given angle $\theta_l$ where the line passes through the point $(x_n, y_n)$. Each line through the point $(x_n, y_n)$ transforms to a unique point in Hough space denoted by $(r_k, \theta_l)$. To implement the transform with a computer, it is necessary to choose an angle increment $\Delta\theta$ and a radius increment $\Delta r$. By incrementing the angle over the range $[0, \pi/2]$ in steps of $\Delta\theta$, $\theta_l$, in Equation 3 is replaced with $i\Delta\theta$ where i is an integer from 1 to $\theta_l/\Delta\theta$ inclusive. $r_k$ is quantized to a step $\Delta r$. Each transformed line is then recorded by incrementing coordinates in an initialized array corresponding to $(r_k, \theta_l)$ The Hough space is a histogram, each point or bin contains the number of pixels that lie on the line represented by the polar coordinates of that bin.

Once the Hough transform has been computed on the edge points, the straight lines representing the suitcase edges are identified. Any points in Hough space with value greater than or equal to a predetermined value, $N_{votes}$, are candidates for lines in image space. However, this procedure does not single out four separate sides as in an ideal case with perfectly straight sides—more than one point in Hough space is left to represent each side of the sliced phantom.

Multiple points in the Hough transform can represent the same edge of the phantom in image space, due to computational errors in reconstruction and image analysis. Identifying groups of points in Hough space is performed by a series of center of mass operations on cluster points: the combinations of points in Hough space.

Every cluster point has both a radius and angle neighborhood which determine the clusters that will be combined. The neighborhoods for radius, $\Delta r_c$ and angle $\Delta\theta_c$ are defined as follows:

$$\frac{\Delta r_c^2}{l^2} < \varepsilon_r \tag{4}$$

-continued $$\frac{\Delta \theta_c^2}{l^2} < \varepsilon_0 \quad (5)$$

where I is the intensity of the cluster point: the number of clusters combined into the cluster point. The purpose of the linear proportionality between neighborhood and intensity, is to prevent a single cluster from growing into the entire image.

Each cluster of intensity H(i,j) has an effective neighborhood radius of $H(i,j)\sqrt{\varepsilon_r}$ in r and $H(i,j)\sqrt{\varepsilon_\theta}$ in θ. Any cluster that lies within another cluster's radius and angle neighborhood will be combined with the first cluster as follows:

$$\begin{pmatrix} i_{new} \\ j_{new} \end{pmatrix} = \frac{1}{I_n + I_m} \left[ I_n \begin{pmatrix} i_n \\ j_n \end{pmatrix} + I_m \begin{pmatrix} i_m \\ j_m \end{pmatrix} \right] \quad (6)$$

$$I_{new} = I_n + I_m \quad (7)$$

where $I_n$ represents the intensity at point $(i_n, j_n)$, $I_m$ represents the intensity at the point $(i_m, j_m)$, and $I_{new}$ represents the intensity at the point $(i_{new}, j_{new})$. The coordinates $(i_n, j_n)$ and $(i_m, j_m)$ are the coordinates of the two clusters being combined, and the coordinates of the resultant cluster are $(i_{new}, j_{new})$.

Once $H(i_{new}, j_{new})$ is computed as described in Equations (6) and (7), the two original clusters, $H(i_n, j_n)$ and $H(i_m, j_m)$, are set to zero. Every time two clusters are combined, their intensities are added to give the new cluster more weight. It is important to recompute the new intensity after every nonzero cluster is added, to facilitate the growing neighborhood.

Once the clusters have been combined as described above, a final thresholding operation is performed. In one experimental application of this approach, after averaging the cluster point, it was found that more than four clusters remain in the image. It was determined experimentally that the leftover clusters often represent lines passing through handles or corners of the case. Therefore, any clusters that are created from less than 6 original clusters are ignored.

Once the Hough transform has been computed, and the number of cluster points has been reduced in number, the equations of the lines are computed from the cluster coordinates. The angle in Hough space represents the angle from the origin of a normal to the line, not the angle of the line.

The normalization procedure is carried out as follows:

$$\theta_{image} = \begin{cases} \theta_{hough} - \frac{3\pi}{2} & \text{if } \theta_{hough} > \frac{3\pi}{4} \\ \theta_{hough} + \frac{\pi}{2} & \text{if } \theta_{hough} < -\frac{\pi}{4} \\ \theta_{hough} - \frac{\pi}{2} & \text{otherwise} \end{cases} \quad (8)$$

where $\theta_{hough}$ is the angle coordinate of the cluster in Hough space and $\theta_{image}$ is the angle, relative to the vertical axis, of the line in image space the cluster represents. This gives straight line equations for the IQP suitcase walls.

Block 806 represents finding the corners of the IQP sides. This is accomplished using the straight line equations found in the step described by Block 805. The intersection of non-parallel lines are found. If the above steps return four lines, the method of the present invention determines if they represent the sides of the IQP within the chosen slice. A total of six line pairs can be formed from the four lines. For each line pair, the difference in the line angle $\theta_{image}$ is computed.

If exactly four line pairs are apart by more than some threshold for parallel lines, $\theta_\parallel$ two line pairs must be apart by less than $\theta_\parallel$. This indicates a four sided polygon has been found with opposite sides that are less than $\theta_\parallel$ apart. All other cases are errors, and are reported to the user.

If four sides are found, they are reordered counter-clockwise beginning with the right side. The lower right coordinate is designated $x_o, y_o$ and the upper right is designated $x_3, y_3$. Ordering is done so that the corners may be referenced later. If more sides are found, the phantom is considered to be partially outside the field of view.

Figure 9:
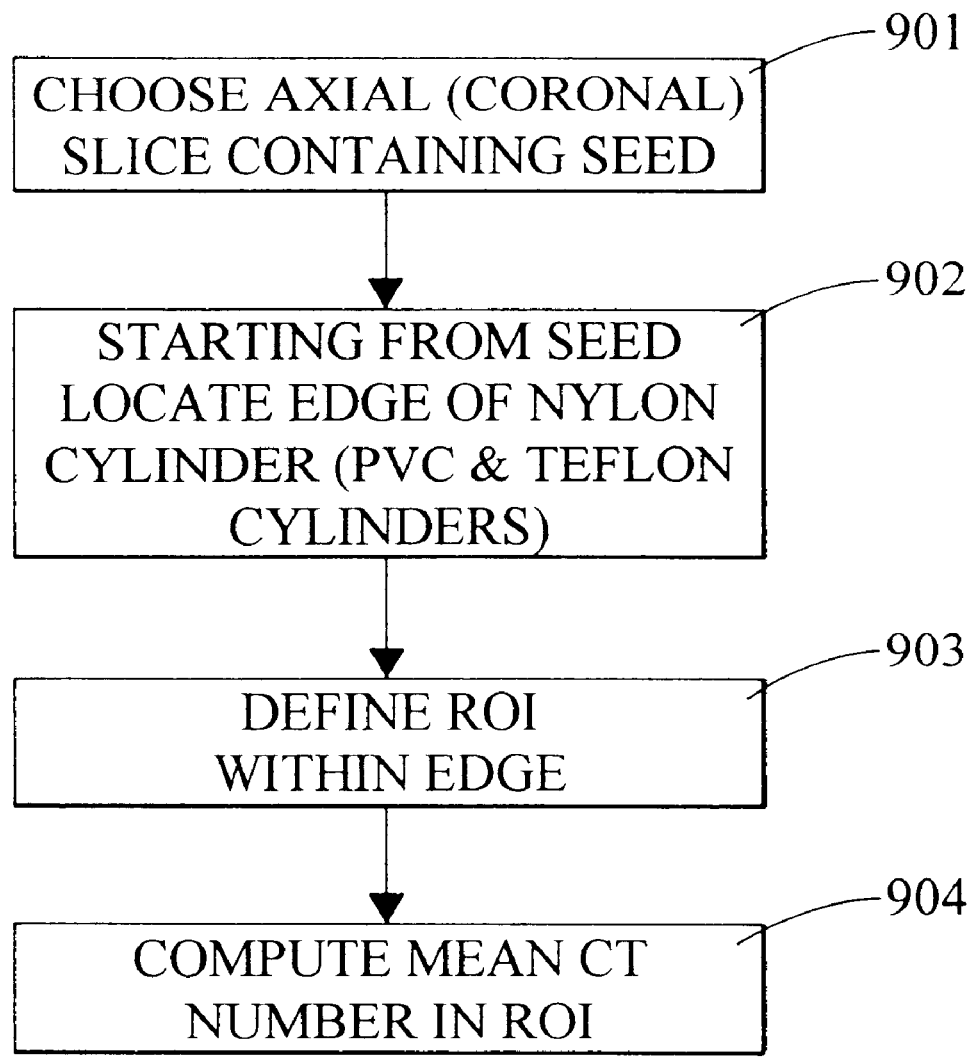
FIG. 9 is a logical flow diagram of one embodiment of how a Nylon cylinder is located in the phantom, how. the region of interest (hereinafter "ROI") is identified, and the mean CT number is calculated.

FIG. 9 represents a preferred embodiment of block 703 of FIG. 7. The Nylon cylinder is located within an axial slice in the phantom, and an ROI is identified. The Nylon cylinder is located with an initial estimate of the location of the center of the cylinder. This estimate is called the seed. The seed is calculated from the knowledge of the phantom and its position within the FOV. The seed voxel coordinates are $(x_s, y_s, z_s)$. In block 901, the axial slice containing the seed is determined. In the axial slice intersecting the seed voxel, the steps below are followed.

1. In accordance with block 902, starting at the seed voxel, at coordinates $(x_s, y_s, z_s)$, search right in the axial slice until a pixel with CT number value below the predefined threshold, $\rho_{obj}$, is found. The last pixel above the threshold, $\rho_{obj}$, is on the object edge. Note that the edge is part of the object.
2. In accordance with block 902, trace a clockwise path around the object edge storing the coordinates of pixels along the path in an array. A pixel is considered part of the object if its CT number value is greater than $\rho_{obj}$. Since all edge pixels are edge connected, the next pixel belonging to the path can only fall in three places. If the edge adjacent positions are searched in a clockwise order, beginning 90 degrees counter-clockwise of the last direction traveled, a clockwise path is traced around the object. (e.g., If one moves down from the last pixel in the path to the current pixel, the first neighbor checked is right of the current pixel.)
3. For the first pixel only, start the clockwise search of neighbors in the same direction as the search for the edge.

The edge points are then averaged to find a geometric center in the axial slice. Next, the sagittal slice intersecting this center point is chosen for similar edge search. The depth coordinates in this slice are then averaged and combined with the axial slice results to give the center coordinates $(i_c, j_c, k_c)$.

Block 903 represents finding the ROI within the nylon object. A voxel with coordinates (i,j,k) is considered to be within the elliptical ROI if the following condition is met:

$$\frac{(i - i_c)^2}{a^2} + \frac{(j - j_c)^2}{b^2} \leq 1 \quad k = k_c \quad (9)$$

As the pixels within ROI are found, their CT number values are stored in an array and a running count is kept of the number of pixels inside the ROI.

Block 904 represents the calculation of the mean value from the ROI. The mean value inside the ROI is computed from the pixel values that were stored during the search process. The mean value is then computed as follows:

$$\mu_{ROI} = \frac{1}{N_A} \sum_{n=1}^{N_A} \rho_n \qquad (10)$$

where $N_A$ is the number of pixels in the ROI and $\rho_n$ is the CT number value of the $n^{th}$ pixel. The standard deviation within the ROI is:

$$\sigma_{ROI} = \sqrt{\frac{1}{N_A} \sum_{n=1}^{N_A} (\rho_n - \mu_{ROI})^2} \qquad (11)$$

where $\rho_n$ is the CT number value of the $n^{th}$ pixel.

The PVC and Teflon cylinder centers are located as in the process described in FIG. 9. The only difference is that coronal slices are selected to identify the PVC and Teflon cylinders (as indicated in the parentheses in FIG. 9).

The standard deviation of the difference of two image slices is taken to be the measure of image noise. The noise is computed in this manner because artifacts that are generated by the reconstruction algorithm are deterministic, and do not provide information about the X-ray emission of the scanner, but do contribute to the standard deviation measurement. Therefore, artifacts are a source of error in the measurement of noise. Pairs of slices that use data from successive rotations (no common data) are identified. The difference image of a pair of slices is created by subtracting the CT numbers in corresponding voxels of the pair, and inserting the difference value in a corresponding voxel in the difference image. Multiple difference images are made. The mean and standard deviation in the difference images is calculated. Due to inhomogeneities in the nylon, and due to the modulation created by the reconstruction algorithm, each image slice in the nylon may not have the same mean CT number value. Therefore, the mean values of the difference images will be different. For the noise measurement to be meaningful, the most suitable difference image is selected by the following method.

1. On the first measured difference image, the mean and standard deviation are recorded, and the difference image is considered the current selection.
2. The next difference image is created using a pair of slices shifted by one pixel along the z-axis from the position of the previous pair. Each successive difference image replaces the previously selected one if either of the following two statements is true.
   The absolute value of the mean is within a predefined range and the standard deviation is less than the last recorded standard deviation.
   The absolute value of the mean is within the predefined range and the last recorded mean absolute value is not within the predefined range.
3. The process is repeated a predetermined number of times, the number of times being selected based on the length of the Nylon cylinder.

For the difference image thus selected, the mean and standard deviation values are compared with predetermined threshold values. If the absolute values of either measure exceed the threshold values, the scanner fails the test.

The reason that pairs that are one rotation apart are chosen is twofold. First, the slices that are one rotation apart are made by data from the same gantry angles. Therefore the artifacts are similar and can be subtracted out, so that photon noise can be estimated accurately.

Second, in slices that are one rotation apart, the data used to reconstruct the slices comes from separate rotations. Therefore, the data are statistically independent, and the noise can be computed using a simple difference computation. If the data to make the slices are common, the difference alone does not provide the full information about X-ray flux. In that case, the difference measure must be adjusted to account for correlated noise.

Due to the fact that precise positioning is not possible, the Nylon phantom is made with a large diameter, so that the slices can be subtracted leaving a sufficient ROI for the noise measurement. Also, due to the fact that the slices are apart by one rotation, the Nylon cylinder is made long enough that the slice spacing exists for several slice pairs.

Figure 10:
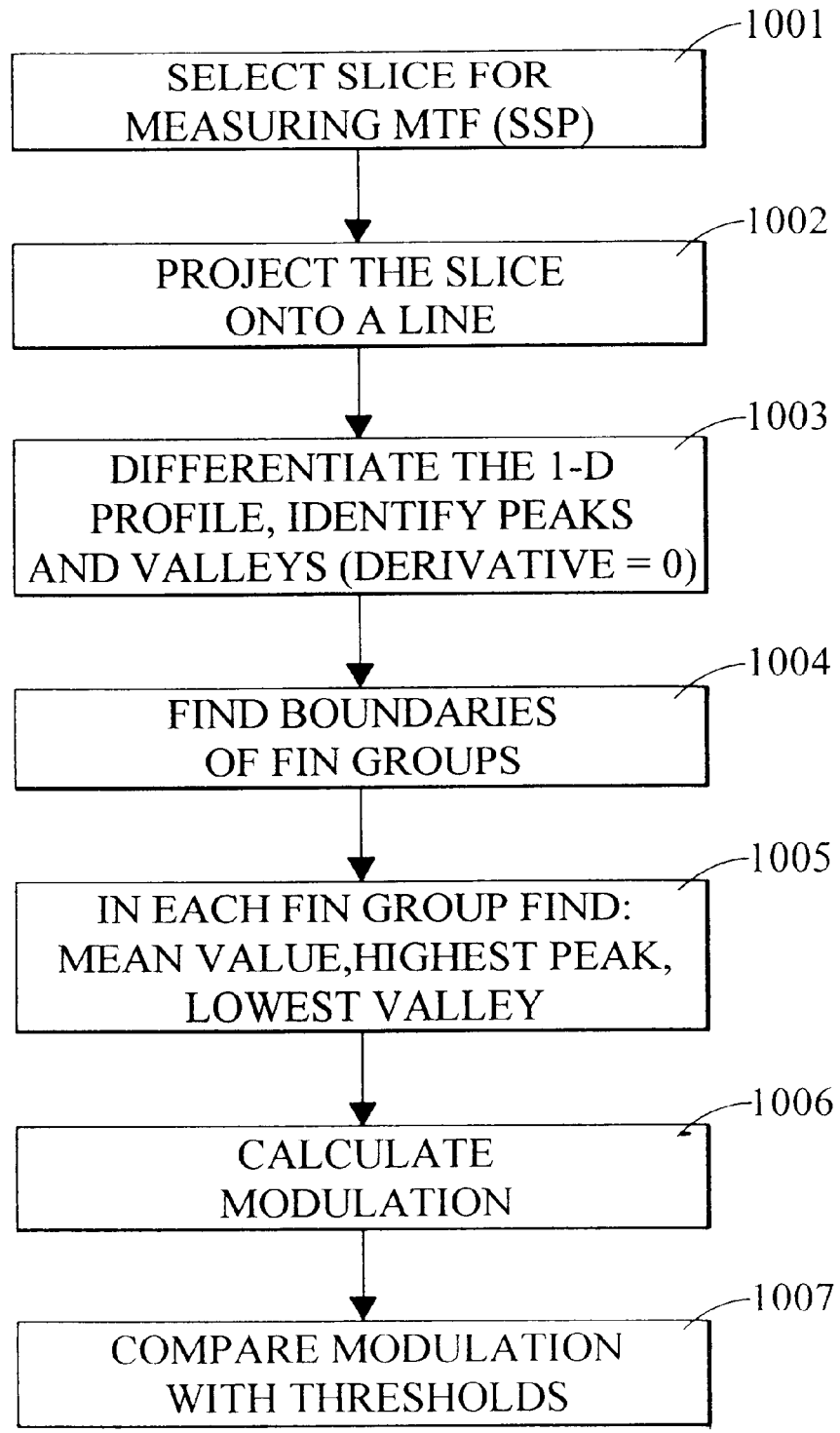
FIG. 10 is one embodiment of a logical flow diagram for measuring the MTF (SSP).

Referring to FIG. 10, in the calculation of MTF, and SSP, comb phantoms are used. The comb phantoms have groups of plastic fins. The groups are separated by gaps. A fin group is a number of fins with a spacing between the fins equal to the width of a fin. A fin group represents a spatial frequency measured in line pairs per unit length. The spacing between groups is larger than the spacing between two fins, so that boundaries between groups can be identified. The measurement of MTF and SSP is as follows.

As indicated in Block 1001, a slice through the comb phantom is chosen. The slice is an axial slice in the case of MTF measurement, and a sagittal slice in SSP measurement but the method of measurement is the same.

1. As indicated in Block 1002, density values are projected onto the coordinate axis which is generally aligned with the length of the comb phantom, to form a 1-D projection. The reason that density values are projected as opposed to using a 1-D profile, is that if the suitcase is tilted, then the profile may pass though air.
2. As indicated in Block 1003, peaks and valleys are found in the 1-D projection. The peaks and valleys are computed as local maxima and minima. Differentiation gives maxima and minima as the points with zero derivative.
3. In Block 1004, the boundaries of the fin groups, $i_{min}^n$ and $i_{max}^n$ are determined for a group number n.
4. Next, as indicated in Block 1005, the mean projection value for each group of fins is found using the following equation (12).

$$\overline{P}_n = \frac{1}{i_{max}^n - i_{min}^n + 1} \sum_{i=i_{min}^n}^{i_{max}^n} P(i). \qquad (12)$$

5. Finding the highest peak in the group and the lowest valley in the group:

$$P_{max}^n = \max_{i_{min}^n \leq i \leq i_{max}^n} P(i) \qquad (13)$$

$$P_{min}^n = \max_{i_{min}^n \leq i \leq i_{max}^n} P(i) \qquad (14)$$

6. As indicated in Block 1006, the values of the valley are subtracted from the peak, and the difference is divided by the mean value of the group to find the percent modulation, $M_n$, as follows:

$$M_n = \frac{P_{max}^n - P_{min}^n}{\overline{P}_n} \times 100\% \qquad (15)$$

As indicated in Block 1007, the percentage modulation is compared with a threshold value. If the modulation is greater than a minimum value for each group of fins, the scanner passes the MTF test.

A region growing algorithm is used to emulate the detection of objects by the AD software. Because all objects in the IQP have known locations relative to the case center, it is possible to predefine seed voxel locations that will fall within objects. From here it is possible to use region growing coupled with erosion and dilation techniques to find the density and mass of chosen objects.

As the object is grown, the number of every current voxel's neighboring voxels in C(i,j,k) in the density range $\rho_{min\_E}$ to $\rho_{max\_E}$ are counted. If the number of neighboring object voxels is less than $N_{nbr}$, the current voxel's address is stored to be eroded in a first pass.

Once the region growing is complete, all voxels marked to be eroded in the first pass are removed from the label array. A second pass of erosion is then performed on the label array using the same criteria: any voxels in the label image that have less than $N_{nbr}$ neighbors in the density range $\rho_{min\_E}$ to $\rho_{max\_E}$ are marked for erosion and removed from the label array.

Once the object had been successfully eroded as described above, the CT number values of all voxels remaining in the label image are used to compute the mean of the eroded object. The mean value, denoted the core mean value, is computed as follows:

$$\mu_{core} = \frac{1}{N_C} \sum_{n=1}^{N_C} \rho_n \quad (16)$$

where $N_C$ is the number of pixels in the eroded object and $\rho_n$ is the CT number value of the $n^{th}$ pixel within the eroded object.

Once the object is eroded, two passes of dilation are performed so the object mass may be computed. The dilation is performed as follows on the label array:

1. All non-object voxels that neighbor voxels within the object are marked to be added to the object if they are in the density range $\rho_{min\_D}$ to $\rho_{max\_D}$.
2. The voxels marked in step 1 are added to the label image.
3. The process is repeated once.

The voxels added to the object during the dilation process are then used to compute a mean density for the entire dilated object. The equation governing this is the same form as Equation (16):

$$\mu_{label} = \frac{1}{N_D + N_C} \sum_{n=1}^{N_D+N_C} \rho_n \quad (17)$$

where $N_D$ is the number of pixels in the dilated layer, $N_C$ is the number of pixels in the eroded object, and $\rho_n$ is the CT number value of the $n^{th}$ pixel within the labeled object.

Once the core density and labeled object density have been computed, the mass of the object, $M_{object}$, is computed using label image density for the dilated voxel layer.

$$M_{object} = (\mu_{core} N_C + \mu_{label} N_D) V_v \quad (18)$$

where $N_D$ is the number of pixels in the dilated layer, $N_C$ is the number of pixels in the eroded object, and Vv is the voxel volume.

Where multiple phantoms are available, the identity of each phantom can be uniquely identified or encoded by making indentations in at least one of the inserts contained in each phantom, and preferably along the perimeter of the sheet insert of each phantom.

Throughout the description of the invention it is noted that many thresholds, such as density thresholds, mass thresholds, and difference thresholds as well as process parameters are used to carry out the various methods of the invention. These thresholds and parameters are determined based on measurements and analysis of images from a CT scanner.

While this invention has been particularly shown and described with references to preferred embodiments thereof, it will be understood by those skilled in the art that various changes in form and details may be made therein without departing from the spirit and scope of the invention as defined by the claims below.

The preferred embodiments and claims listed above do not preclude other embodiments of the described invention. For example, the materials used in the testing of the X-ray tube voltage stability may be other materials. The material used in the testing of noise may be water, and scans may be repeated for the noise measurement by subtraction of slices, instead of using a long cylinder. The placement of objects may be varied as long as overlapping objects do not invalidate measurements.

The sizes of the various objects may be changed in other embodiments of the same invention. The fin spacing and number of fin groups may also be changed in other embodiments of the same invention. For example, a single fin group may be used for a test with the binary result of pass or fail.

In order to find the suitcase corners, other algorithms may be employed, for example, a grey scale Hough transform may be employed after using region-growing in the preferred embodiment to find the walls. Alternatively, a function fitting could be employed, for example, by minimizing the least-squares error of a line.

The order of the tests may be changed.

The use of the AD software is optional in other embodiments. Also, the test can be accomplished manually, volumetric data are not required, and the scanning does not have to be helical.

What is claimed is:

1. A method of assessing performance of a computed tomography (CT) scanner including a scanner axis of rotation, comprising:
    (a) using the scanner to scan a phantom in one or more of its normal modes of operation;
    (b) reconstructing a three-dimensional volume CT image for a region containing at least a portion of the phantom;
    (c) calculating properties of the CT image; and
    (d) using the calculated properties of the CT image to assess CT scanner performance;
    wherein the CT scanner includes a translator that translates the phantom substantially in the same direction as the scanner axis of rotation while operating the scanner to scan the phantom.

2. The method of claim 1, wherein calculating properties of the CT image is performed automatically.

3. The method of claim 1, wherein calculating properties of the CT image is performed manually.

4. The method of claim 1, wherein using the scanner to scan a phantom comprises acquiring CT projection data simultaneously with phantom translation.

5. The method of claim 1, wherein using the scanner to scan a phantom comprises displacing the phantom along the scanner axis of rotation at a sequence of successive fixed axial positions, and acquiring a set of CT projection data at each position.

6. The method of claim 1, wherein using the scanner to scan a phantom further comprises generally aligning the phantom with the scanner axis of rotation.

7. The method of claim 1, wherein the CT scanner has a single fixed mode of reconstructing a three-dimensional volume CT image.

8. The method of claim 1, wherein the phantom is a container with a plurality of inserts disposed therein.

9. The method of claim 8, wherein the inserts are positioned at predetermined locations within the phantom.

10. The method of claim 8, wherein portions of at least two inserts are positioned so as to overlap in the same CT image.

11. The method of claim 8, wherein portions of at least two inserts are positioned so as to overlap in the same CT axial image.

12. The method of claim 8, wherein the container is made of plastic material such that
    (a) the container does not require careful handling;
    (b) the number of metallic components in the container is minimized, so as to minimize CT reconstruction artifacts.

13. The method of claim 8, wherein foam is used to position and maintain the inserts separate from one another within the container.

14. The method of claim 8, wherein calculating properties of the CT image further comprises
    (a) identifying a plurality of volume elements in the CT image, each volume element being associated with a density value;
    (b) combining the volume elements into objects;
    (c) associating the objects with phantom inserts; and
    (d) calculating properties of the objects.

15. The method of claim 14, wherein combining the volume elements into objects further comprises using region growing.

16. The method of claim 14, wherein combining the volume elements into objects further comprises using connected components labeling (CCL).

17. The method of claim 14, wherein the CT scanner includes an in-plane, and calculating properties of the objects further comprises measuring the in-plane resolution of the CT scanner.

18. The method of claim 17, wherein measuring the in-plane resolution of the CT scanner comprises:
    (a) mounting a comb insert inside the phantom so that it is scanned generally perpendicular to the scanner axis of rotation, said insert including a plurality of fin groupings;
    (b) calculating CT number variation within at least one of the fin groupings;
    (c) comparing the CT number variation to a reference value so as to determine the response of the CT scanner to the spatial frequency represented by the at least one fin grouping.

19. The method of claim 14, wherein calculating properties of the objects further comprises measuring the axial resolution of the CT scanner.

20. The method of claim 19, wherein measuring the axial resolution of the CT scanner comprises:
    (a) mounting a comb insert inside the phantom so that it is scanned generally parallel to the scanner axis of rotation, the insert including a plurality of fin groupings;
    (b) calculating CT number variation within at least one of the fin groupings;
    (c) comparing the CT number variation to a reference value so as to determine the response of the CT scanner to the spatial frequency represented by the at least one fin grouping.

21. The method of claim 14, wherein calculating properties of the objects further comprises associating a characteristic CT number with an insert associated with each object.

22. The method of claim 21 wherein associating the characteristic CT number of each insert is the mean CT number of all the volume elements comprising the insert.

23. The method of claim 21, wherein assigning a characteristic CT number with an insert comprises:
    (a) identifying a region of interest within the corresponding object;
    (b) calculating the mean CT number of all the volume elements within the region of interest.

24. The method of claim 21, further comprising comparing the differences in said characteristic CT numbers of at least two inserts to a reference value so as to assess scanner CT number uniformity.

25. The method of claim 24, wherein at least two inserts are placed at different locations within the CT scanner field of view.

26. The method of claim 24, wherein at least two inserts are placed at different locations along the scanner axis of rotation.

27. The method of claim 21, further comprising comparing the ratios of the characteristic CT numbers of at least two inserts to a reference value so as to assess the scanner CT number linearity.

28. The method of claim 27, wherein at least two inserts are made of different materials.

29. The method of claim 27, wherein at least two inserts are of different size.

30. The method of claim 14, wherein calculating properties of the objects further comprises measuring image noise.

31. The method of claim 30, wherein measuring image noise comprises:
    (a) identifying a region of interest within an object;
    (b) calculating standard deviation of CT numbers within said region of interest;
    (c) comparing the standard deviation to a reference value so as to assess the image noise of the CT scanner.

32. The method of claim 30, further including translating the phantom with the translator when scanning the phantom, wherein the insert associated with at least one object has a length greater than the distance traveled by the phantom in one rotation of the gantry of the CT scanner, and measuring the image noise comprises:
    (a) selecting an axial slice of the at least one object;
    (b) identifying a region of interest within the at least one object;
    (c) subtracting the selected axial slice from an axial slice located a predetermined number of slices away from the selected slice, thereby creating a difference image;
    (d) calculating standard deviation of CT numbers within said region of interest in the difference image;
    (e) comparing the standard deviation to a reference value so as to assess the image noise of the CT scanner.

33. The method of claim 14, further comprising selecting a plurality of fiducial marks in the CT image of the phantom.

34. The method of claim 33, wherein said fiducial marks are selected from the plurality of volume elements associated with the container.

35. The method of claim 33, wherein the translator is a conveyor, and the phantom is supported on the conveyor as the phantom is translated through the scanner, the method further comprising:

calculating relative coordinates of the fiducial marks so as to determine:
(a) the position;
(b) the slope; and
(c) the translational speed of the conveyor.

36. The method of claim 8, wherein the calculation of the properties of the CT image is automatically done on a separate automatic diagnostics computer configured to perform automatic diagnostics.

37. The method of claim 36, wherein said automatic diagnostics is configured for explosive detection.

38. The method of claim 36, wherein said automatic diagnostics is configured for medical scanning.

39. The method of claim 36, wherein at least one insert is to test a property of the automatic diagnostics.

40. The method of claim 36, wherein the plurality of inserts includes at least one simulated sheet explosive.

41. The method of claim 36, wherein the plurality of inserts includes at least one simulated bulk explosive.

42. The method of claim 8, wherein each insert is characterized by a predetermined shape and density.

43. The method of claim 8, wherein the plurality of inserts includes:
(a) one or more comb inserts;
(b) a diagonal rod;
(c) a Nylon cylinder;
(d) a PVC cylinder; and
(e) a Teflon cylinder.

44. The method of claim 8, further comprising inferring the identity of the phantom.

45. The method of claim 44, wherein inferring the identity of the phantom comprises modifying at least one insert in a manner unique to each phantom.

46. The method of claim 45, wherein modifying at least one insert comprises making one or more indentations in at least one insert.

47. The method of claim 44, wherein CT performance is assessed in a manner unique to each phantom.

48. The method of claim 8, wherein calculating properties of the CT image further comprises
(a) identifying a plurality of volume elements in the CT image, each volume element being associated with a density value;
(b) combining the volume elements into objects;
(c) associating the objects with phantom inserts; and
(d) calculating properties of the objects.

49. The method of claim 1, further comprising:
(a) computing the distance between the center of the phantom and the scanner axis of rotation;
(b) comparing the distance to a predetermined reference value;
(c) declaring the CT image of the phantom unsuitable for assessing performance of the CT scanner if the distance exceeds the predetermined reference value.

50. The method of claim 1, further comprising:
(a) computing the angle between the phantom and the scanner axis of rotation;
(b) comparing the angle to a predetermined reference value;
(c) declaring the CT image of the phantom unsuitable for assessing performance of the CT scanner if the angle exceeds the predetermined reference value.

51. The method of claim 1, wherein the phantom is a container with a plurality of inserts, and further including using at least one insert to test communication between the CT scanner and an automatic diagnostics computer.

52. The method of claim 51, wherein using at least one insert to test communication between the CT scanner and the automatic diagnostics computer comprises:
(a) identifying the volume elements in the CT image corresponding to the at least one. insert;
(b) establishing contiguity of any of the identified volume elements;
(c) declaring a communication error if the identified volume elements are not contiguous.

53. The method of claim 51, wherein the at least one insert is a diagonal rod.

54. A method of assessing performance of a computed tomography (CT) scanner comprising:
using the scanner (a) to scan a phantom in one or more of its normal modes of operation while translating said phantom along the scanner axis of rotation and (b) to produce scanned data of the phantom, and assessing the performance of the scanner from the scanned data.

55. The method according to claim 54, wherein using the scanner to scan a phantom and to produce scanned data comprises reconstructing a three-dimensional volume CT image for a region containing at least a portion of the phantom and calculating the properties of the CT image, and assessing the performance of the scanner comprises assessing the performance of the scanner from assessing the predetermined properties of the CT image.

56. A computed tomography (CT) scanner including a scanner axis of rotation including apparatus for assessing the performance of the scanner, comprising:
a translator for translating a phantom through the scanner substantially in the same direction as the scanner axis of rotation while operating the scanner in one or more of its normal modes of operation; and
a processor constructed and arranged so as to (a) reconstruct a three-dimensional volume CT image for a region containing at least a portion of the phantom scanned by the scanner while operating the scanner in one or more of its normal modes of operation; (b) provide information for calculating properties of the CT image; and (c) use of the calculated properties of the CT image to assess CT scanner performance.

57. The scanner of claim 56, wherein the processor calculates properties of the CT image automatically.

58. The scanner of claim 56, wherein the properties of the CT image is calculated manually.

59. The scanner of claim 56, wherein the scanner scans the phantom so as to acquire CT projection data simultaneously with phantom translation.

60. The scanner of claim 56, wherein the translator displaces the phantom along the scanner axis of rotation at a sequence of successive fixed axial positions, and a set of CT projection data is acquired at each position.

61. The scanner of claim 56, wherein the scanner scans the phantom while the phantom is generally aligned with the scanner axis of rotation.

62. The scanner of claim 56, wherein scanner includes a single fixed mode of reconstructing a three-dimensional volume CT image.

63. The scanner of claim 56, wherein the phantom is a container with a plurality of inserts disposed therein.

64. The scanner of claim 63, wherein the inserts are positioned at predetermined locations within the phantom.

65. The scanner of claim 63, wherein portions of at least two inserts are positioned so as to overlap in the same CT image.

66. The scanner of claim 63, wherein portions of at least two inserts are positioned so as to overlap in the same CT axial image.

67. The scanner of claim 63, wherein the container is made of plastic material such that
 (a) the container does not require careful handling;
 (b) the number of metallic components in the container is minimized, so as to minimize CT reconstruction artifacts.

68. The scanner of claim 63, wherein foam is used to position and maintain the inserts separate from one another within the container.

69. The scanner of claim 63, wherein the processor further:
 (a) identifies a plurality of volume elements in the CT image, each volume element being associated with a density value;
 (b) combines the volume elements into objects;
 (c) associates the objects with phantom inserts; and
 (d) calculates properties of the objects.

70. The scanner of claim 69, wherein the processor combines the volume elements using region growing.

71. The scanner of claim 69, wherein the processor combines the volume elements into objects using connected components labeling (CCL).

72. The scanner of claim 69, wherein the CT scanner includes an in-plane, and the processor calculates properties of the objects by measuring the in-plane resolution of the CT scanner.

73. The scanner of claim 72, wherein the processor measures the in-plane resolution of the CT scanner by:
 (a) mounting a comb insert inside the phantom so that it is scanned generally perpendicular to the scanner axis of rotation, said insert including a plurality of fin groupings;
 (b) calculating CT number variation within at least one of the fin groupings;
 (c) comparing the CT number variation to a reference value so as to determine the response of the CT scanner to the spatial frequency represented by the at least one fin grouping.

74. The scanner of claim 69, wherein the processor measures the axial resolution of the CT scanner.

75. The scanner of claim 74, wherein the axial resolution of the CT scanner is measured by:
 (a) mounting a comb insert inside the phantom so that it is scanned generally parallel to the scanner axis of rotation, the insert including a plurality of fin groupings;
 (b) calculating CT number variation within at least one of the fin groupings;
 (c) comparing the CT number variation to a reference value so as to determine the response of the CT scanner to the spatial frequency represented by the at least one fin grouping.

76. The scanner of claim 69, wherein the processor associates a characteristic CT number with an insert associated with each object.

77. The scanner of claim 76, wherein the characteristic CT number associated with each insert is the mean CT number of all the volume elements comprising the insert.

78. The scanner of claim 76, wherein the processor assigns a characteristic CT number with an insert by:
 (a) identifying a region of interest within the corresponding object; and
 (b) calculating the mean CT number of all the volume elements within the region of interest.

79. The scanner of claim 76, wherein the processor compares the differences in the characteristic CT numbers of at least two inserts to a reference value so as to assess scanner CT number uniformity.

80. The scanner of claim 79, wherein at least two inserts are placed at different locations within the CT scanner field of view.

81. The scanner of claim 79, wherein at least two inserts are placed at different locations along the scanner axis of rotation.

82. The scanner of claim 76, wherein the processor compares the ratios of the characteristic CT numbers of at least two inserts to a reference value so as to assess the scanner CT number linearity.

83. The scanner of claim 82, wherein at least two inserts are made of different materials.

84. The scanner of claim 82, wherein at least two inserts are of different size.

85. The scanner of claim 69, the processor measures image noise.

86. The scanner of claim 85, the processor measures image noise by:
 (a) identifying a region of interest within an object;
 (b) calculating standard deviation of CT numbers within the region of interest;
 (c) comparing the standard deviation to a reference value so as to assess the image noise of the CT scanner.

87. The scanner of claim 85, wherein the insert associated with at least one object has a length greater than the distance traveled by the phantom in one rotation of the gantry of the CT scanner, and the processor measures the image noise by:
 (a) selecting an axial slice of the at least one object;
 (b) identifying a region of interest within the at least one object;
 (c) subtracting the selected axial slice from an axial slice located a predetermined number of slices away from the selected slice, thereby creating a difference image;
 (d) calculating standard deviation of CT numbers within said region of interest in the difference image; and
 (e) comparing the standard deviation to a reference value so as to assess the image noise of the CT scanner.

88. The scanner of claim 69, further comprising a plurality of fiducial marks selected in the CT image of the phantom.

89. The scanner of claim 88, wherein the fiducial marks are selected from the plurality of volume elements associated with the container.

90. The scanner of claim 88, wherein the translator is a conveyor, and the phantom is supported on the conveyor as the phantom is translated through the scanner, where in the processor:
 calculates relative coordinates of the fiducial marks so as to determine:
  (a) the position;
  (b) the slope; and
  (c) the translational speed of the conveyor.

91. The scanner of claim 63, further including a separate automatic diagnostics computer configured to calculate properties of the CT image automatically done on the automatic diagnostics computer.

92. The scanner of claim 91, wherein said automatic diagnostics computer is configured for explosive detection.

93. The scanner of claim 91, wherein said automatic diagnostics computer is configured for medical scanning.

94. The scanner of claim 91, wherein at least one insert is to test a property of the automatic diagnostics.

95. The scanner of claim 91, wherein the plurality of inserts includes at least one simulated sheet explosive.

96. The scanner of claim 91, wherein the plurality of inserts includes at least one simulated bulk explosive.

97. The scanner of claim 63, wherein each insert is characterized by a predetermined shape and density.

98. The scanner of claim 63, wherein the plurality of inserts includes:

(a) one or more comb inserts;

(b) a diagonal rod;

(c) a Nylon cylinder;

(d) a PVC cylinder; and (e) a Teflon cylinder.

99. The scanner of claim 63, wherein the processor infers the identity of the phantom.

100. The scanner of claim 99, wherein at least one insert in a manner is modified to be unique within the phantom so as inferring the identity of the phantom.

101. The scanner of claim 100, the one insert is modified by making one or more indentations in at least one insert.

102. The scanner of claim 99, wherein CT performance is assessed in a manner unique to each phantom.

103. The scanner of claim 63, wherein the processor:

(a) identifies a plurality of volume elements in the CT image, each volume element being associated with a density value;

(b) combines the volume elements into objects;

(c) associates the objects with phantom inserts; and (d) calculates properties of the objects.

104. The scanner of claim 56, wherein the processor:

(a) computes the distance between the center of the phantom and the scanner axis of rotation;

(b) compares the distance to a predetermined reference value;

(c) declares the CT image of the phantom unsuitable for assessing performance of the CT scanner if the distance exceeds the predetermined reference value.

105. The scanner of claim 56, wherein the processor:

(a) computes the angle between the phantom and the scanner axis of rotation;

(b) compares the angle to a predetermined reference value; and (c) declares the CT image of the phantom unsuitable for assessing performance of the CT scanner if the angle exceeds the predetermined reference value.

106. The scanner of claim 56, wherein the phantom is a container with a plurality of inserts, wherein at least one insert is configured to test communication between the CT scanner and an automatic diagnostics computer.

107. The scanner of claim 106, wherein the processor tests communication between the CT scanner and the automatic diagnostics computer by:

(a) identifying the volume elements in the CT image corresponding to the at least one insert;

(b) establishing contiguity of any of the identified volume elements; and (c) declaring a communication error if the identified volume elements are not contiguous.

108. The scanner of claim 106, wherein the at least one insert is a diagonal rod.

109. A CT scanner configured to assess its own performance, the scanner comprising:

a translator for conveying a phantom through the scanner along the scanner axis of rotation while operating the scanner in one or more of its normal modes of operation, and a processor for receiving scanned data of the phantom during a scan of the phantom, and assessing the performance of the scanner from the scanned data.

110. The CT scanner according to claim 109, wherein the processor is configured to reconstruct a three-dimensional volume CT image for a region containing at least a portion of the phantom and calculate the properties of the CT image, and the processor assesses the performance of the scanner from assessing the predetermined properties of the CT image.

* * * * *